United States Patent
Hirai et al.

(10) Patent No.: US 10,786,276 B2
(45) Date of Patent: Sep. 29, 2020

(54) MEDICAL DEVICE

(71) Applicant: OLYMPUS CORPORATION, Hachioji-shi, Tokyo (JP)

(72) Inventors: Yuji Hirai, Sagamihara (JP); Yukihiko Sawada, Yoshikawa (JP); Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 325 days.

(21) Appl. No.: 15/728,947

(22) Filed: Oct. 10, 2017

(65) Prior Publication Data
US 2018/0042638 A1 Feb. 15, 2018

Related U.S. Application Data

(63) Continuation of application No. PCT/JP2016/061376, filed on Apr. 7, 2016.

(30) Foreign Application Priority Data

Apr. 10, 2015 (JP) .................................. 2015-081067

(51) Int. Cl.
*A61B 17/32* (2006.01)
*A61B 90/00* (2016.01)

(52) U.S. Cl.
CPC ...... *A61B 17/320092* (2013.01); *A61B 17/32* (2013.01); *A61B 2017/320074* (2017.08);
(Continued)

(58) Field of Classification Search
CPC ........... A61B 17/320092; A61B 2017/320074; A61B 2017/320094; A61B 2017/320095;
(Continued)

(56) References Cited

U.S. PATENT DOCUMENTS 5,322,055 A * 6/1994 Davison ......... A61B 17/320068
601/2
5,954,736 A * 9/1999 Bishop ........... A61B 17/320092
606/157
(Continued)

FOREIGN PATENT DOCUMENTS

CN 101765495 A 6/2010
JP H09-98979 A 4/1997
(Continued)

OTHER PUBLICATIONS

Oct. 10, 2017 International Preliminary Report on Patentability issued in International Patent Application No. PCT/JP2016/061376.
(Continued)

*Primary Examiner* — Katrina M Stransky
(74) *Attorney, Agent, or Firm* — Oliff PLC

(57) ABSTRACT

A medical device includes, a vibration transmitting member configured to be capable of transmitting vibration for use in a treatment; a jaw configured to move between an abutted position where the jaw abuts on the vibration transmitting member, and a spaced position where the jaw is spaced apart from the vibration transmitting member; and a cover provided in such a position that the vibration transmitting member is interposed between the cover and the jaw, and configured such that a first distal portion, which is located at a distal end of the cover, comes in contact with the vibration transmitting member, when the jaw is located in the abutted position.

7 Claims, 20 Drawing Sheets

(52) U.S. Cl.
CPC ............. *A61B 2017/320088* (2013.01); *A61B 2017/320093* (2017.08); *A61B 2017/320094* (2017.08); *A61B 2017/320095* (2017.08); *A61B 2090/08021* (2016.02)

(58) Field of Classification Search
CPC ....... A61B 2017/320093; A61B 2017/320088; A61B 17/320068
See application file for complete search history.

(56) References Cited

U.S. PATENT DOCUMENTS

| | | | |
|---|---|---|---|
| 6,278,218 B1 * | 8/2001 | Madan ............ | A61B 17/320068 310/312 |
| 6,283,981 B1 * | 9/2001 | Beaupre ......... | A61B 17/320068 606/169 |
| 6,309,400 B2 * | 10/2001 | Beaupre ......... | A61B 17/320068 606/169 |
| 6,325,811 B1 * | 12/2001 | Messerly ....... | A61B 17/320092 606/169 |
| 2006/0264750 A1 | 11/2006 | Yamada et al. | |
| 2008/0234710 A1 * | 9/2008 | Neurohr ......... | A61B 17/320068 606/169 |
| 2009/0030311 A1 | 1/2009 | Stulen et al. | |
| 2009/0036914 A1 | 2/2009 | Houser | |
| 2013/0103065 A1 | 4/2013 | Timm et al. | |
| 2015/0297289 A1 | 10/2015 | Hirai et al. | |

FOREIGN PATENT DOCUMENTS

| | | |
|---|---|---|
| JP | 2001-353165 A | 12/2001 |
| JP | 2002-85420 A | 3/2002 |
| JP | 2002-224133 A | 8/2002 |
| JP | 2005-224585 A | 8/2005 |
| JP | 2010-522034 A | 7/2010 |
| JP | 2010-534525 A | 11/2010 |
| JP | 2010-535087 A | 11/2010 |
| JP | 2013-085963 A | 5/2013 |
| JP | 2014-311 A | 1/2014 |
| JP | 2014-121618 A | 7/2014 |
| WO | 2013/190937 A1 | 12/2013 |
| WO | 2014/078548 A2 | 5/2014 |
| WO | 2014/196641 A1 | 12/2014 |
| WO | 2015/020147 A1 | 2/2015 |

OTHER PUBLICATIONS

Mar. 28, 2017 Office Action issued in Japanese Patent Application No. 2017-501432.
Jul. 25, 2017 Office Action issued in Japanese Patent Application No. JP 2017-501432.
Oct. 10, 2018 Search Report issued in European Patent Application No. 16776616.1.
Jul. 5, 2016 International Search Report issued in International Patent Application No. PCT/JP2016/061376.
Jan. 30, 2019 extended Search Report issued in European Patent Application No. 16776616.1.
Sep. 20, 2019 Office Action issued in Chinese Patent Application No. 201680021193.6.
Jun. 17, 2020 Office Action issued in Chinese Patent Application No. 201680021193.6.

* cited by examiner

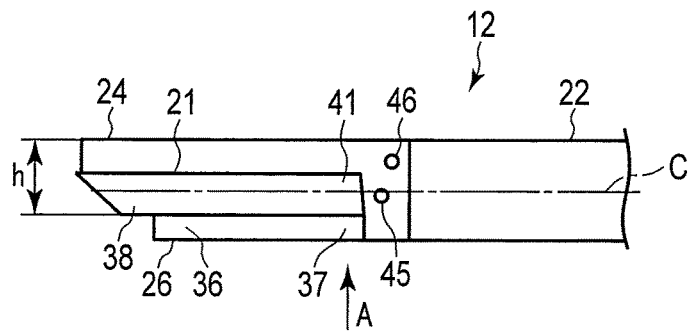
F I G. 9
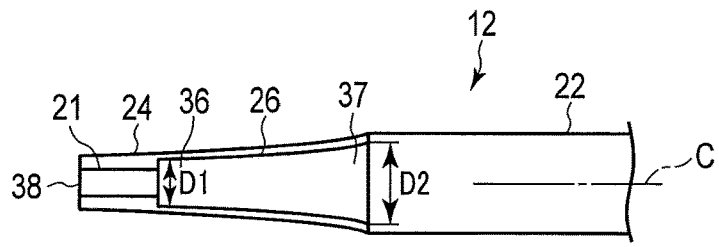
F I G. 10
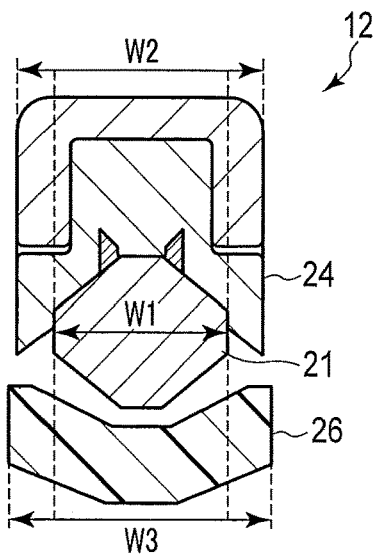
F I G. 11

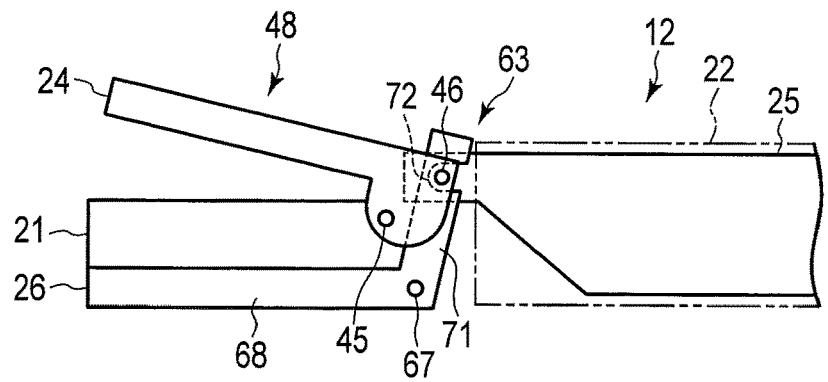
F I G. 21
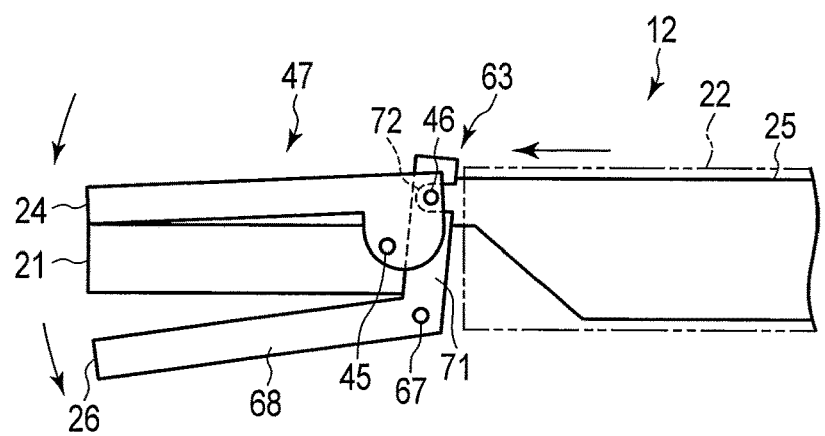
F I G. 22
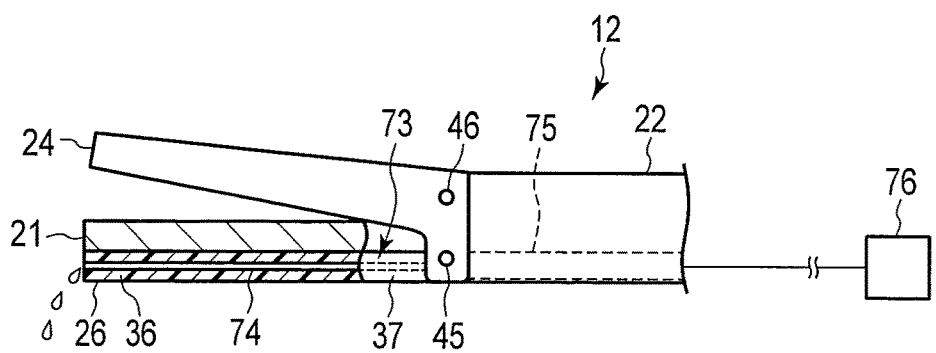
F I G. 23

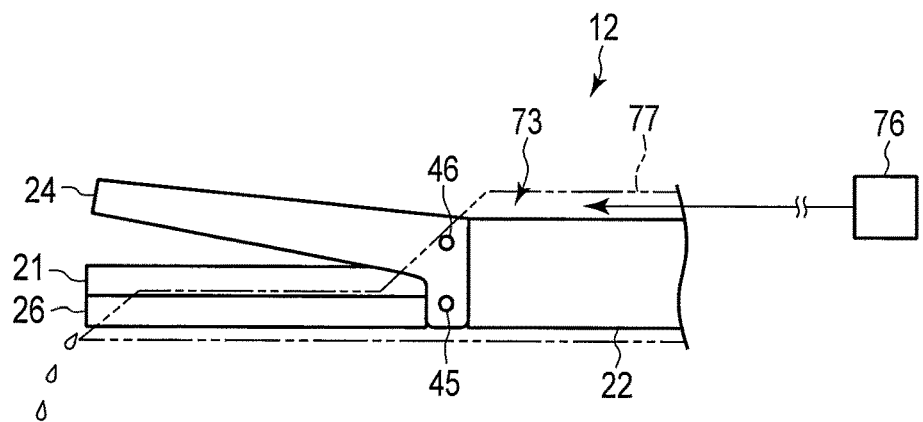
F I G. 24
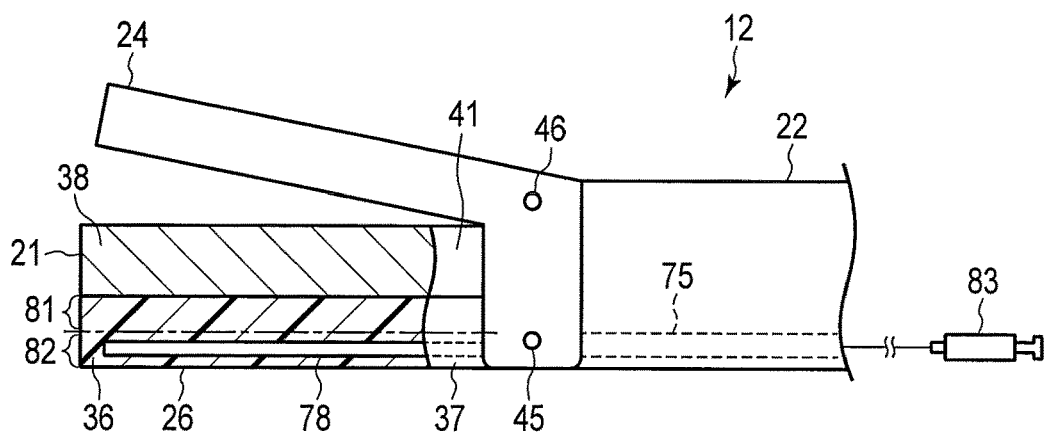
F I G. 25A
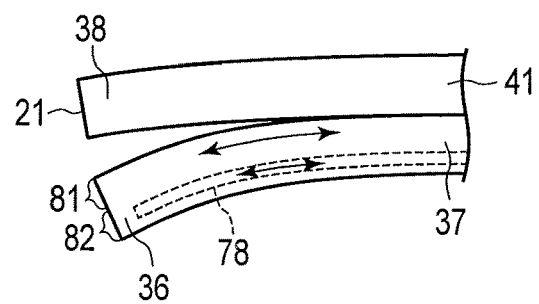
F I G. 25B

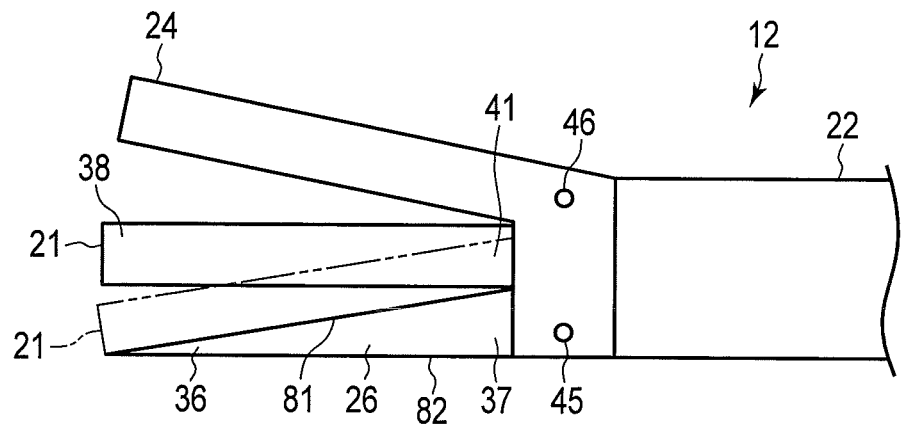
F I G. 26A
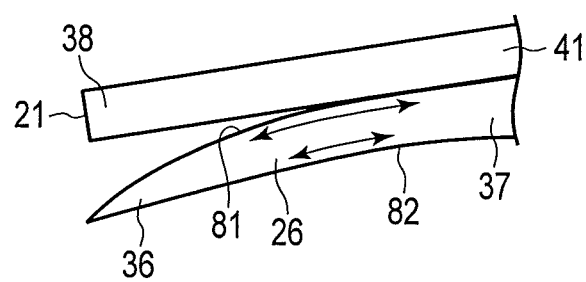
F I G. 26B

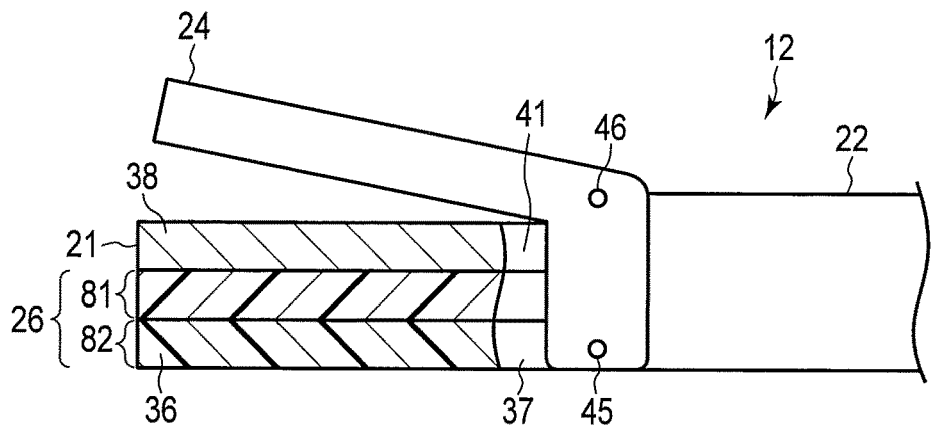
F I G. 27A
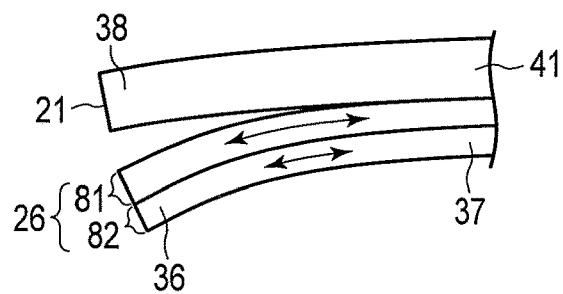
F I G. 27B
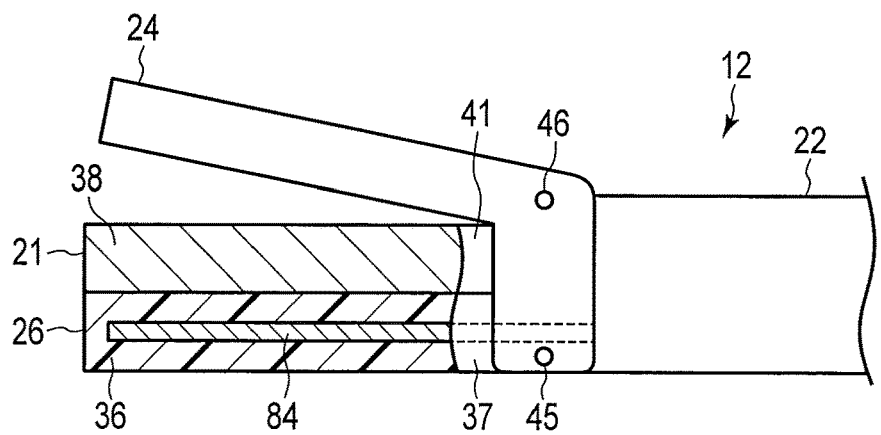
F I G. 28

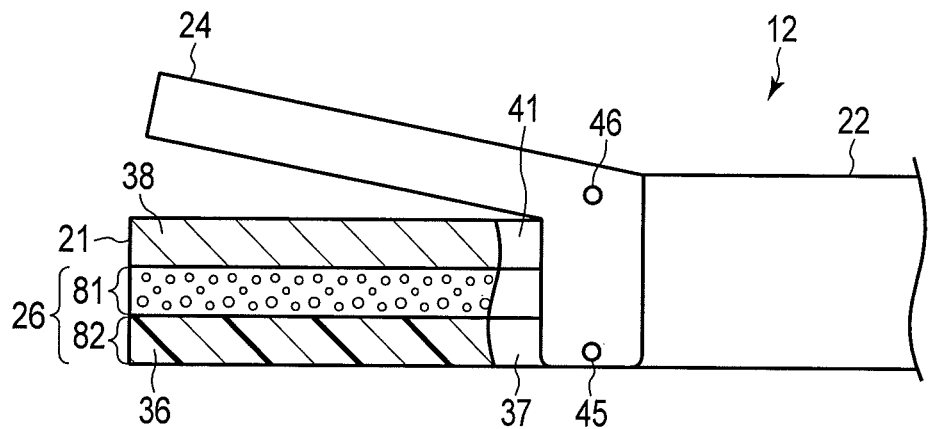
F I G. 29
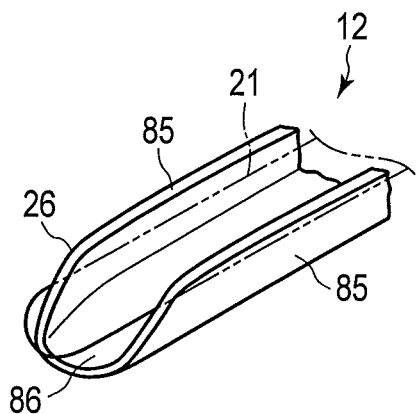
F I G. 30A
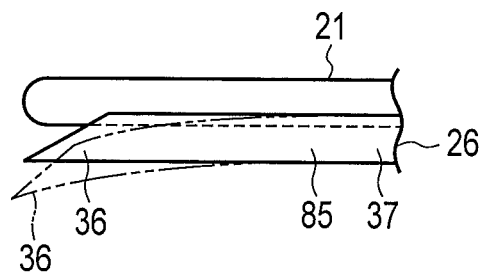
F I G. 30B

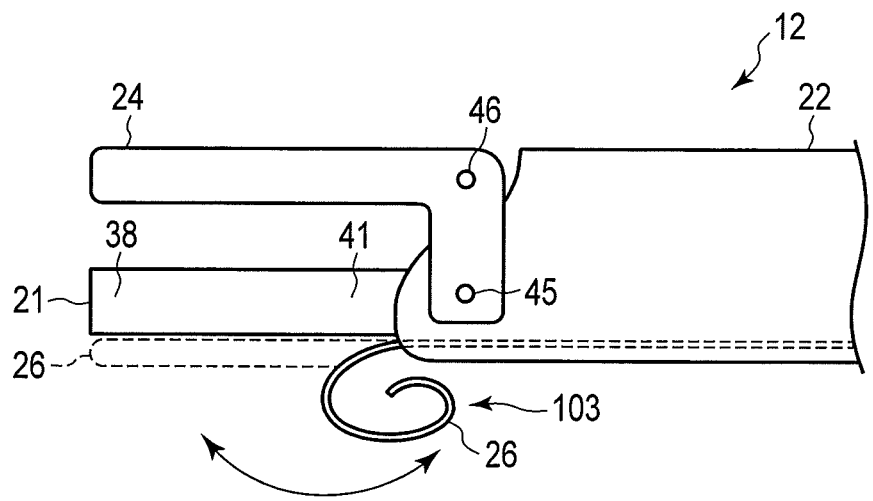
F I G. 37
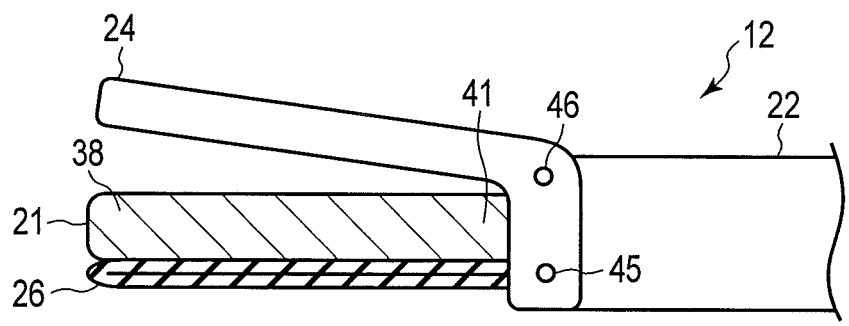
F I G. 38A
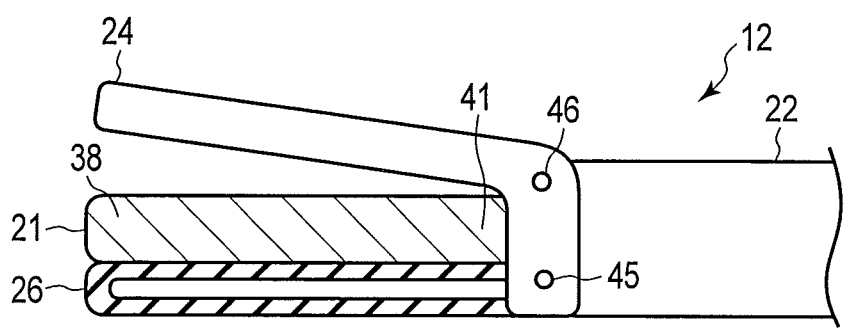
F I G. 38B

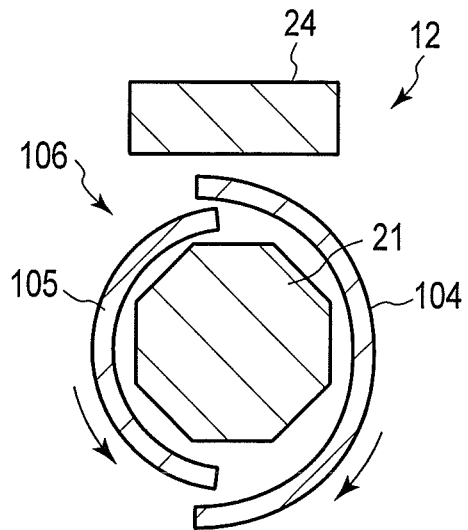
F I G. 39A
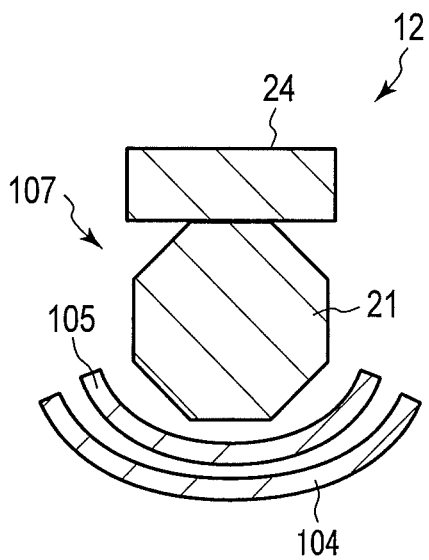
F I G. 39B

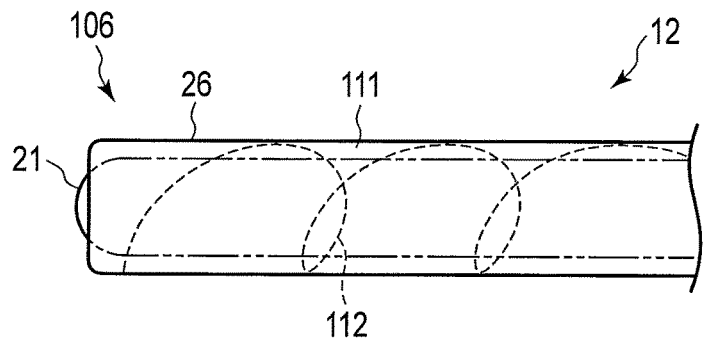
F I G. 40A
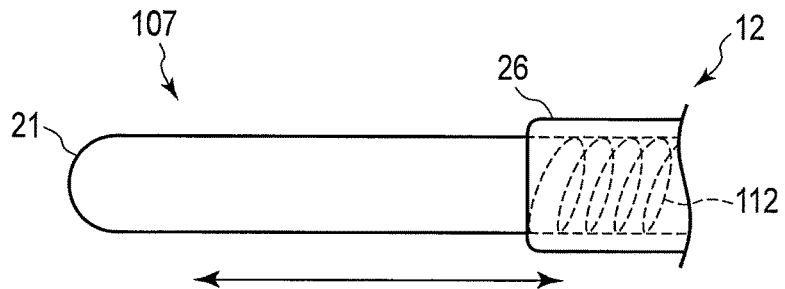
F I G. 40B
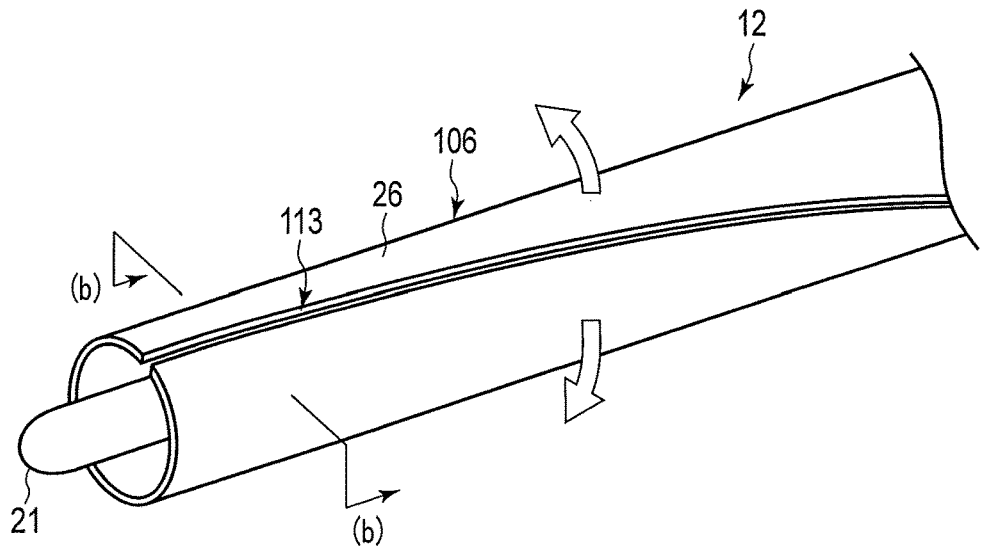
F I G. 41A

MEDICAL DEVICE

CROSS-REFERENCE TO RELATED APPLICATIONS

This application is a Continuation Application of PCT Application No. PCT/JP2016/061376, filed Apr. 7, 2016 and based upon and claiming the benefit of priority from prior Japanese Patent Application No. 2015-081067, filed Apr. 10, 2015, the entire contents of all of which are incorporated herein by reference.

BACKGROUND OF THE INVENTION

1. Field of the Invention

The present invention relates to a medical device which treats body tissue with ultrasonic vibration.

2. Description of the Related Art

Jpn. Pat. Appln. KOKAI Publication No. H9-98979 (patent document 1) discloses an ultrasonic treatment device. In this ultrasonic treatment device, a guard member is provided on a side opposite to a coagulation surface which coagulates body tissue. The guard member can prevent body tissue from being erroneously cauterized at the position thereof.

Jpn. Pat. Appln. KOKAI Publication No. 2014-121618 (patent document 2) discloses an ultrasonic treatment instrument. This ultrasonic treatment instrument includes a vibration transmitting member, a jaw which clamps body tissue between the jaw and the vibration transmitting member, and a vibration transmitting member cover which is located on a side opposite to the jaw and covers the vibration transmitting member. The purpose of use of the vibration transmitting member cover is the same as that of the guard member.

Jpn. Pat. Appln. KOKAI Publication No. 2014-311 (patent document 3) discloses an ultrasonic treatment instrument. This ultrasonic treatment instrument includes a vibration transmitting member, a jaw which clamps body tissue between the jaw and the vibration transmitting member, and a cooling mechanism for cooling the vibration transmitting member after the completion of an ultrasonic treatment. When the cooling mechanism is not used, the cooling mechanism can be evacuated toward a proximal direction of the vibration transmitting member.

BRIEF SUMMARY OF THE INVENTION

In order to achieve the above object, a medical device according to one embodiment of the invention includes a vibration transmitting member configured to be capable of transmitting vibration for use in a treatment; a jaw configured to move between an abutted position where the jaw abuts on the vibration transmitting member, and a spaced position where the jaw is spaced apart from the vibration transmitting member; and a cover provided in such a position that the vibration transmitting member is interposed between the cover and the jaw, and configured such that a first distal portion, which is located at a distal end of the cover, comes in contact with the vibration transmitting member, when the jaw is located in the abutted position.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 9 is a side view illustrating a vibration transmitting member, a jaw and a cover of a medical device of a fifth embodiment.

FIG. 10 is a bottom view illustrating the medical device shown in FIG. 9, as viewed in a direction of an arrow A.

FIG. 11 illustrates a medical device of a sixth embodiment, FIG. 11 being a cross-sectional view illustrating a cross section of the vibration transmitting member, jaw and cover at a position corresponding to a position of line F7-F7 in FIG. 5.

FIG. 21 is a side view illustrating a vibration transmitting member, a jaw and a cover of a medical device of a twelfth embodiment.

FIG. 22 is a side view illustrating a state in which the jaw shown in FIG. 21 is moved to an abutted position.

FIG. 23 is a partially broken-out side view illustrating a vibration transmitting member, a jaw and a cover of a medical device of a 13th embodiment.

FIG. 24 is a side view illustrating a vibration transmitting member, a jaw and a cover of a medical device of a first modification of the 13th embodiment.

FIG. 25A is a side view illustrating a vibration transmitting member, a jaw and a cover of a medical device of a 14th embodiment.

FIG. 25B is a schematic view illustrating a state in which the cover is bent.

FIG. 26A is a side view illustrating a vibration transmitting member, a jaw and a cover of a medical device of a 15th embodiment.

FIG. 26B is a schematic view illustrating a state in which the cover is bent.

FIG. 27A is a side view illustrating a vibration transmitting member, a jaw and a cover of a medical device of a 16th embodiment.

FIG. 27B is a schematic view illustrating a state in which the cover is bent.

FIG. 28 is a partially broken-out side view illustrating a vibration transmitting member, a jaw and a cover of a medical device of a 17th embodiment.

FIG. 29 is a partially broken-out side view illustrating a vibration transmitting member, a jaw and a cover of a medical device of an 18th embodiment.

FIG. 30A is a perspective view illustrating a vibration transmitting member and a cover of a medical device of a 19th embodiment.

FIG. 30B is a schematic side view illustrating a state in which the cover is bent.

FIG. 37 is a side view illustrating a vibration transmitting member, a jaw and a cover of a medical device of a 26th embodiment.

FIG. 38A is a partially broken-out side view illustrating a vibration transmitting member, a jaw and a cover of a medical device of a 27th embodiment.

FIG. 38B is a side view illustrating a state in which the cover of FIG. 38A is swollen.

FIG. 39A is a partially broken-out cross-sectional view illustrating a vibration transmitting member, a jaw, and a cover in a storage position of a medical device of a 28th embodiment.

FIG. 39B is a cross-sectional view illustrating a state in which the cover of FIG. 38A is moved to an exposure position.

FIG. 40A illustrates a first modification of the medical device of the 28th embodiment, FIG. 40A being a side view illustrating the cover in the storage position.

FIG. 40B is a side view illustrating a state in which the cover of FIG. 40A is moved to the exposure position.

FIG. 41A illustrates a second modification of the medical device of the 28th embodiment, FIG. 41A being a perspective view illustrating the cover in the storage position.

DETAILED DESCRIPTION OF THE INVENTION

First Embodiment

A first embodiment of a medical device of the present invention will be described with reference to FIG. 1 to FIG. 5.

Figure 1:
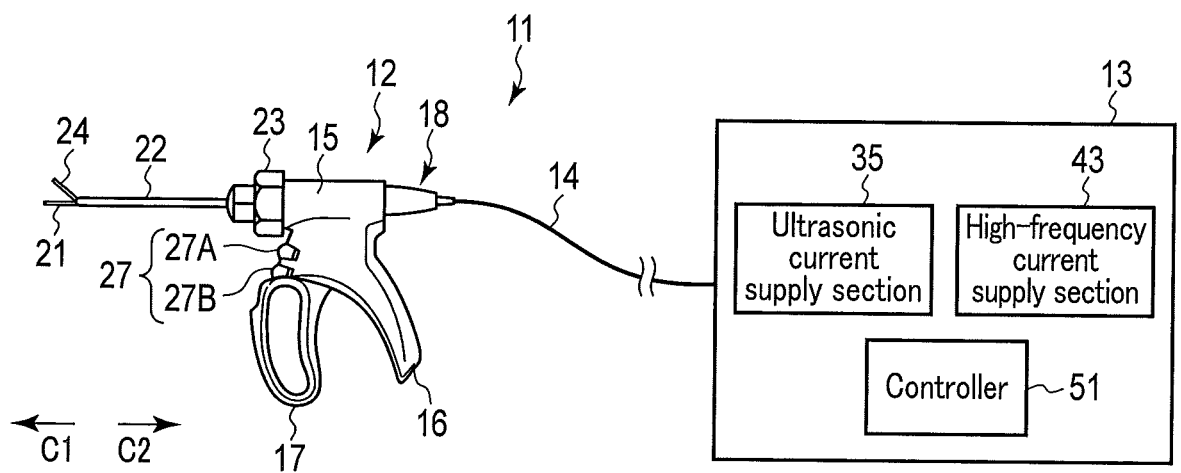
FIG. 1 is a schematic view illustrating the entire configuration of a medical device of a first embodiment.

As illustrated in FIG. 1, a medical device 11 includes a handpiece 12, an electric power source unit 13, and a cable 14 which connects the handpiece 12 and electric power source unit 13.

Figure 2:
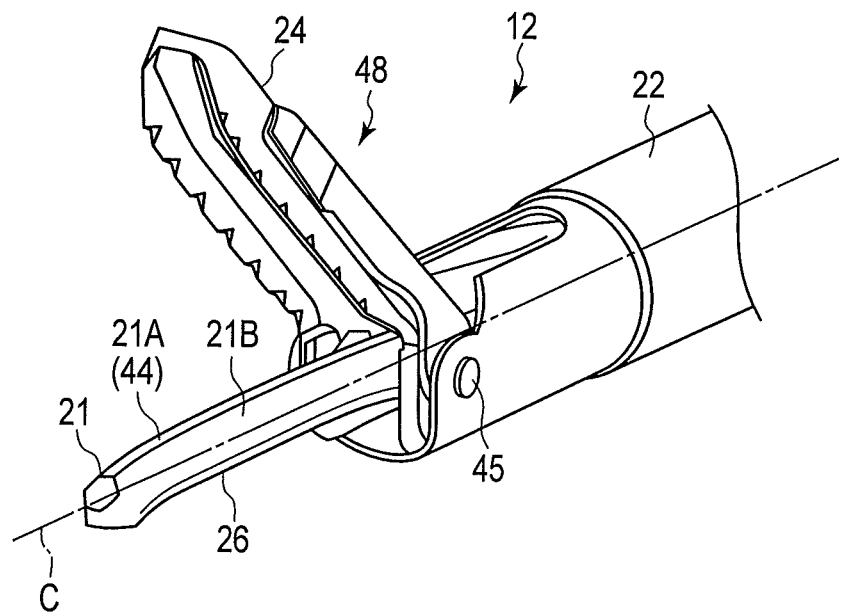
FIG. 2 is a perspective view illustrating a distal portion of a vibration transmitting member and a jaw of the medical device shown in FIG. 1.
Figure 3:
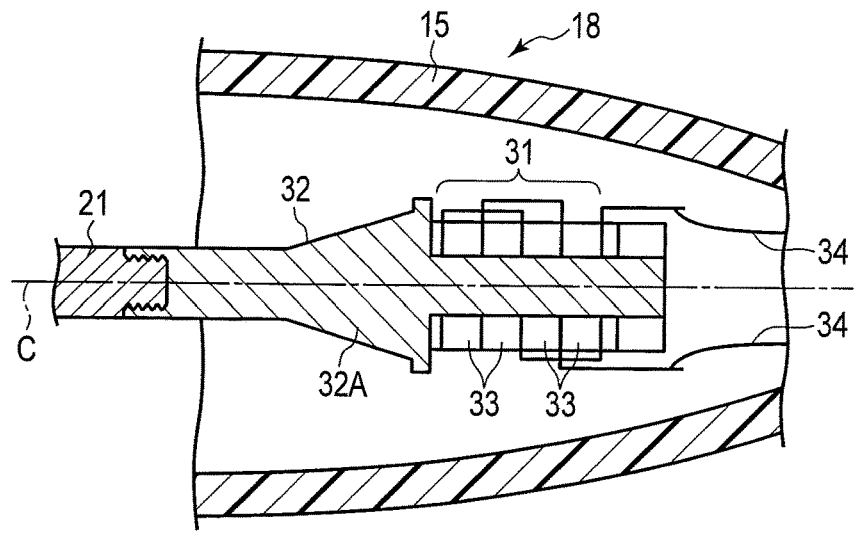
FIG. 3 is a cross-sectional view illustrating a vibration generator of the medical device shown in FIG. 1.

As illustrated in FIG. 1 to FIG. 3, the handpiece 12 includes a held section 15 which constitutes an outer shell; a stationary handle 16 which is fixedly provided on the held section 15; a movable handle 17 which is rotatable relative to the held section 15; a vibration generator 18 (transducer) which is stored in the held section 15; a rod-shaped vibration transmitting member (probe) 21 which is connected to the vibration generator 18; a cylindrical sheath 22 which covers the periphery of the vibration transmitting member 21 and protects the vibration transmitting member 21; a knob 23 (rotary knob) which is fixed to the sheath 22; a jaw 24 which is provided to be rotatable relative to the vibration transmitting member 21 and sheath 22; a cylindrical driving pipe 25 (see FIG. 4) which is provided in the inside of the sheath 22 and is advanced and retreated when the jaw 24 is opened and closed; and a cover 26 which is provided in such a position that the vibration transmitting member 21 is interposed between the cover 26 and the jaw 24. In the present embodiment, one of two directions, which are parallel to a longitudinal direction C of the vibration transmitting member 21, is defined as a distal direction C1, and the direction opposite to the distal direction is defined as a proximal direction C2.

The held section 15 is provided with two energy operation input buttons 27. By operating the two energy operation input buttons 27, a surgeon can apply energy (ultrasonic vibration and high-frequency current) to body tissue that is a treated target via the vibration transmitting member 21. A first energy operation input button 27A corresponds to a so-called coagulation mode, and executes an output of ultrasonic energy and high-frequency energy, which are suited to coagulation of body tissue and sealing of a blood vessel. A second energy operation input button 27B corresponds to a so-called coagulation/incision mode, and executes an output of ultrasonic energy and high-frequency energy, which are suited to coagulation and incision of body tissue, or sealing and incision of a blood vessel.

As illustrated in FIG. 3, the vibration generator 18 includes an ultrasonic transducer 31 and a horn member 32. The ultrasonic transducer 31 is provided with a plurality of piezoelectric elements 33 (four piezoelectric elements 33 in the present embodiment) for changing an electric current into ultrasonic vibration. One end of an electric line 34 is connected to the ultrasonic transducer 31. The electric line 34 extends through the inside of the cable 14, and the other end of the electric line 34 is connected to an ultrasonic current supply section 35 of the electric power supply unit 13. If electric power is supplied from the ultrasonic current supply section 35 to the ultrasonic transducer 31 via the electric line 34, ultrasonic vibration is generated in the ultrasonic transducer 31.

As illustrated in FIG. 3, the ultrasonic transducer 31 is attached to the horn member 32. The horn member 32 is formed of a metallic material. The horn member 32 includes a cross-sectional area transition portion 32A having a substantially conical shape. The cross-sectional area of the cross-sectional area transition portion 32A gradually decreases toward the distal direction C1 of the vibration transmitting member 21. The amplitude of the ultrasonic vibration, which is generated in the ultrasonic transducer 31, is increased in the cross-sectional area transition portion 32A.

Figure 4:
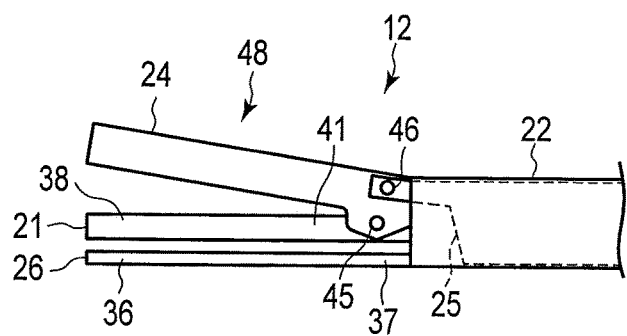
FIG. 4 is a side view illustrating the vibration transmitting member and the jaw in a spaced position, which are shown in FIG. 2.

As illustrated in FIG. 4, the cover 26 includes a first distal portion 36 which is located on a distal side in the longitudinal direction of the vibration transmitting member 21, and a first proximal portion 37 which is located on an opposite side to the first distal portion 36. The cover 26 extends in a tongue shape in a direction along the vibration transmitting member 21. The cover 26 covers that side of the vibration transmitting member 21, which is opposite to the side thereof facing the jaw 24. Specifically, the vibration transmitting member 21 is interposed between the cover 26 and the jaw 24. The cover 26 is formed of a material which is elastically deformable in a manner to follow the bending of the vibration transmitting member 21. The cover 26 is formed of a material, such as a synthetic resin material, which has heat resistance, has a higher adiathermancy than metals or the like, and has a lower thermal conductivity than metals or the like. A small gap is provided between the cover 26 and the vibration transmitting member 21.

As illustrated in FIG. 2, the vibration transmitting member 21 is formed of, for example, a biocompatible metallic material (e.g. a titanium alloy, etc.) in a rod shape. Vibration for use in a treatment can be transmitted to the vibration transmitting member 21. A vibration transmitting member main body 66 of the vibration transmitting member 21 includes a second distal portion 38 which is located on the distal side in the longitudinal direction C thereof, and a second proximal portion 41 which is located on a side (proximal side) opposite to the second distal portion 38. One of two electric lines is connected to the second proximal portion 41. To the vibration transmitting member 21, ultrasonic vibration is transmitted from the vibration generator 18, and a high-frequency current is supplied from a high-frequency current supply section 43. Thus, the vibration transmitting member 21 is capable of not only applying ultrasonic vibration to body tissue, but the vibration transmitting member 21 also functions as one of bipolar electrodes for performing a bipolar treatment. In the meantime, in the present embodiment, one of the second electric lines is electrically connected to a negative electrode of the high-frequency current supply section 43. Thus, the vibration transmitting member 21 constitutes a return electrode in the bipolar treatment.

The vibration transmitting member main body 66 of the vibration transmitting member 21 has, for example, a polygonal cross-sectional shape (e.g. an octagonal cross-sectional shape in the present embodiment). The vibration transmitting member main body 66 includes a treatment surface 21A which is mainly used for incision of body tissue (including a blood vessel, etc.) with ultrasonic vibration, and a seal surface 21B which is inclined to the treatment surface 21A. The seal surface 21B is mainly used for coagulation of body tissue and for sealing of a blood vessel. Two seal surfaces 21B are provided at two locations between which the treatment surface 21A is interposed (see FIG. 7).

As illustrated in FIG. 2 and FIG. 4, the sheath 22 has a cylindrical shape, and protects the vibration transmitting member 21 which is disposed therein. The sheath 22 is attached, at a proximal portion thereof, to the held section 15 in the state in which the sheath 22 is rotatable relative to the held section 15. The knob 23 is provided fixedly to the sheath 22. The sheath 22 includes a support pin 45 at a distal portion thereof. The proximal portion of the sheath 22 is connected to the other of the two second electric lines. The jaw 24 is electrically connected to the sheath 22. Thus, the jaw 24, which is provided at the distal end of the sheath 22, serves as the other of the bipolar electrodes for performing the bipolar treatment. An electrode portion of the jaw 24 is formed of, for example, a copper alloy or the like. In the meantime, in the present embodiment, the other second electric line is electrically connected to the positive electrode of the high-frequency current supply section 43. Thus, the jaw 24 and sheath 22 constitute an active electrode in the bipolar treatment.

The jaw 24 includes an insulating portion 44 which is formed of, for example, a synthetic resin material, and has heat resistance and electrical insulation properties, the insulating portion 44 being located at a position opposed to the vibration transmitting member main body 66. The insulating portion 44 is located in such a position that the insulating portion 44 is abutted on the treatment surface 21A, and pushes and bends the vibration transmitting member main body 66. For example, polyetheretherketone (PEEK) is usable as the material of the insulating portion 44. Besides, the insulating portion 44 may be formed of PTFE, carbon nanotube-containing resin, or other resin material with lubricating properties.

As illustrated in FIG. 4, the driving pipe 25 is provided such that the driving pipe 25 can advance and retreat in the inside of the sheath 22. The driving pipe 25 includes a driving pin 46 for opening and closing the jaw 24.

Figure 5:
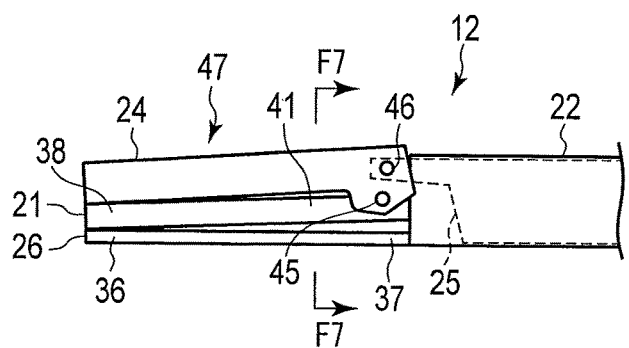
FIG. 5 is a side view illustrating a state in which the jaw shown in FIG. 4 is moved to an abutted position.

As illustrated in FIG. 2, FIG. 4 and FIG. 5, the jaw 24 is supported by the support pin 45 which is fixed to the distal portion of the sheath 22, and is attached so as to be rotatable about the support pin 45. By operating the movable handle 17, the jaw 24 can be moved between an abutted position 47 where the jaw 24 can abut on the vibration transmitting member main body 66 and can grasp body tissue, and a spaced position 48 where the jaw 24 is spaced apart from the vibration transmitting member 21. The jaw 24 is formed in a plate shape having a recess portion for storing the vibration transmitting member main body 66, such that the vibration transmitting member 21 having the octagonal cross section and the above-described insulating portion 44 are engaged with each other. The jaw 24 is formed of a metallic material such as a stainless steel alloy, and operates so as to clamp the insulating portion 44 between the jaw 24 and the vibration transmitting member main body 66.

As illustrated in FIG. 1, the electric power source unit 13 includes the ultrasonic current supply section 35, the high-frequency current supply section 43, and a controller 51 which controls these components. The controller 51 can control the supply of an ultrasonic generating current from the ultrasonic current supply section 35, and the supply of a high-frequency current from the high-frequency current supply section 43. If the energy operation input button 27 is operated by the surgeon, an electric signal is delivered to the controller, and an input of the energy operation is detected. Thereby, the controller 51 supplies an ultrasonic generating current from the ultrasonic current supply section 35 to the vibration transmitting member 21, and supplies a high-frequency current from the high-frequency current supply section 43 to the vibration transmitting member 21.

Referring to FIG. 4 and FIG. 5, the function of the medical device 11 of the present embodiment will be described. Before treating body tissue that is a treated target by using the medical device 11 of the present embodiment, the surgeon secures a path (port) for accessing the treated target, by using a cylindrical guide, such as a trocar, which can penetrate a patient's skin or the like.

The surgeon moves the jaw 24 from the spaced position 48 illustrated in FIG. 4 to the abutted position 47 illustrated in FIG. 5. Thereby, by the urging force (pushing force) of the jaw 24, the vibration transmitting member 21 bends toward the cover 26, and the second distal portion 38 of the vibration transmitting member main body 66 abuts on the first distal portion 36 of the cover 26. In this state, the gap between the second distal portion 38 of the vibration transmitting member main body 66 and the first distal portion 36 of the cover 26 is closed. In this state, the vibration transmitting member main body 66 and jaw 24 are inserted into the guide such as the trocar. At this time, since the resistance force acting on the first distal portion 36 of the cover 26 can be received by the vibration transmitting member 21 side, sharp bending or the like does not occur in the cover 26. Thus, the vibration transmitting member main body 66 and jaw 24 can smoothly reach the region of the treated target.

In the region of the treated target, the surgeon can clamp the body tissue between the vibration transmitting member main body 66 and jaw 24. Furthermore, if the surgeon operates the energy operation input button 27, the surgeon can apply energy to the clamped body tissue. If the second energy operation input button 27B which corresponds to the coagulation/incision mode is operated, the vibration transmitting member 21 performs ultrasonic vibration, and applies thermal energy by frictional movement to the body tissue. At this time, the temperature of the vibration transmitting member 21 rises to, for example, 200° C. or above. Thereby, the body tissue and blood vessel can be incised between the treatment surface 21A of vibration transmitting member main body 66 and the jaw 24. At the same time, a high-frequency current is passed through the body tissue between the seal surface 21B of the vibration transmitting member main body 66 serving as the electrode and the jaw 24, and electric energy can be applied to the body tissue. Thereby, the body tissue and blood vessel can be coagulated.

In this manner, in the present embodiment, two kinds of energies are applied from the vibration transmitting member 21 and the jaw 24. Thereby, the body tissue clamped therebetween can efficiently be coagulated and incised.

In addition, in the state in which the body tissue is clamped between the vibration transmitting member main body 66 and the jaw 24, if the surgeon operates the first energy operation input button 27A, the high-frequency current is passed through the body tissue between the seal surface 21B of the vibration transmitting member main body 66 serving as the electrode and the jaw 24, and electric energy can be applied to the body tissue. Thereby, only the coagulation of the body tissue can be performed.

According to the first embodiment, the medical device 11 includes the vibration transmitting member main body 66 configured to be capable of transmitting vibration for use in a treatment; the jaw 24 configured to move between the abutted position 47 where the jaw 24 abuts on the vibration transmitting member main body 66, and the spaced position 48 where the jaw 24 is spaced apart from the vibration transmitting member main body 66; and the cover 26 provided in such a position that the vibration transmitting member 21 is interposed between the cover 26 and the jaw 24, and configured such that the first distal portion 36, which is located at the distal end of the cover 26, comes in contact with the vibration transmitting member 21, when the jaw 24 is located in the abutted position 47.

According to this configuration, when the jaw 24 is in the abutted position 47, only the first distal portion 36 of the cover 26 abuts on the vibration transmitting member main body 66. Thus, the area where the cover 26 is put in contact with the vibration transmitting member main body 66, that is, the vibration transmitting member 21, can be minimized. Thereby, the amount of heat, which is conducted from the vibration transmitting member main body 66 to the cover 26, can be minimized, and it is possible to prevent the temperature of the cover 26 from rising and adversely affecting the body tissue which is in contact with the cover 26. Moreover, when the vibration transmitting member main body 66 and jaw 24 are inserted from the outside of the body of the patient into the region of the treated target, the cover 26 is not separated from the vibration transmitting member main body 66, and it is possible to prevent a great pressure from acting on the cover 26 and damaging the cover 26. Besides, when the vibration transmitting member main body 66 and jaw 24 are inserted, a large resistance force does not occur, and the labor of the surgeon at the time of surgery can be reduced.

The cover 26 is formed of a material having a high adiathermancy and a low thermal conductivity. According to this configuration, even if the temperature of that surface of the cover 26, which is located on the vibration transmitting member 21 side, rises due to heat from the vibration transmitting member 21, it is possible to prevent as much as possible a temperature rise on the surface of the cover 26 on the side opposite to the vibration transmitting member 21, with which the surgeon's hand, or a body tissue different from the treated target, may possibly come in contact.

The vibration transmitting member main body 66 bends by being pushed by the jaw 24 which is in the abutted position 47, and comes in contact with the first distal portion 36 of the cover 26. According to this configuration, the cover 26 can be separated from the vibration transmitting member main body 66 unless where necessary, and it is possible to prevent as much as possible the conduction of the heat of the vibration transmitting member 21 to the cover 26 side.

Second Embodiment

Figure 6:
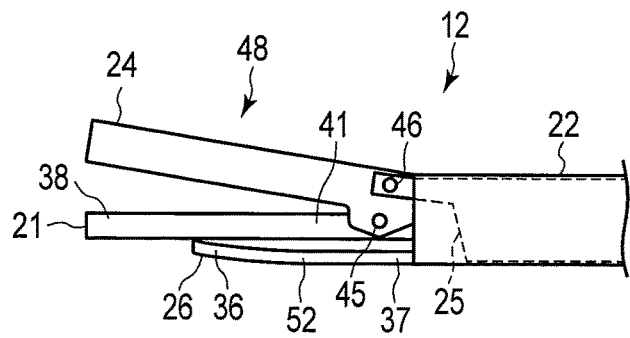
FIG. 6 is a side view illustrating a vibration transmitting member, a jaw and a cover of a medical device of a second embodiment.

Referring to FIG. 6, a medical device of a second embodiment will be described. A medical device 11 of the second embodiment differs from that of the first embodiment in that the shape of the cover 26 is different. However, the other parts are common to the first embodiment. Thus, the different part from the first embodiment will mainly be described, and an illustration or description of the parts common to the first embodiment is omitted.

The cover 26 includes a first distal portion 36 which is located on the distal side in the longitudinal direction C of the vibration transmitting member 21, a first proximal portion 37 which is located on the opposite side to the first distal portion 36, and a curved portion 52 (an intermediate portion which continuously connects the first proximal portion 37 and first distal portion 36) which is continuous with the first distal portion 36 and first proximal portion 37. The cover 26 is formed of, for example, a synthetic resin material in a tongue shape. The cover 26 covers that side of the vibration transmitting member main body 66, which is opposite to the side thereof facing the jaw 24. The cover 26 is formed of a material which has heat resistance and adiathermancy, and has a lower thermal conductivity than metals or the like.

The first proximal portion 37 is provided such that a gap is created between the first proximal portion 37 and the vibration transmitting member main body 66. The first proximal portion 37 extends in a direction along the direction (longitudinal direction C) in which the vibration transmitting member main body 66 extends. The curved portion 52 is bent in a direction approaching the vibration transmitting member main body 66. The first distal portion 36 abuts on an intermediate part of the vibration transmitting member main body 66. The curved portion 52 (intermediate portion) may be formed in a crank shape between the first proximal portion 37 and first distal portion 36, such that the first distal portion 36 is located at a position of abutment on the vibration transmitting member main body 66.

Referring to FIG. 6, the function of the medical device 11 of the present embodiment will be described. Before treating body tissue that is a treated target by using the medical device 11 of the present embodiment, the surgeon secures a path (port) for accessing the treated target, by using a cylindrical guide, such as a trocar, which can penetrate a patient's skin or the like.

The surgeon moves the jaw 24 from the spaced position 48 to the abutted position 47. In addition, in the present embodiment, the first distal portion 36 of the cover 26 abuts on the vibration transmitting member main body 66 from the beginning. In this state, the gap between the second distal portion 38 of the vibration transmitting member main body 66 and the first distal portion 36 of the cover 26 is closed. In this state, the vibration transmitting member main body 66 and jaw 24 are inserted into the trocar. At this time, since the resistance force acting on the first distal portion 36 of the cover 26 can be received by the vibration transmitting member 21, sharp bending or the like does not occur in the cover 26. Thus, the vibration transmitting member main body 66 and jaw 24 can smoothly reach the region of the treated target.

In the region of the treated target, the surgeon can clamp the body tissue between the vibration transmitting member main body 66 and jaw 24. Furthermore, by operating the energy operation input button 27 in this state, the surgeon can perform, like the first embodiment, the coagulation and incision or only the coagulation of the body tissue and blood vessel.

According to the present embodiment, the cover 26 includes the first proximal portion 37 which is provided in the direction along the vibration transmitting member 21, with the gap being provided between the first proximal portion 37 and the vibration transmitting member main body 66; the first distal portion 36 which abuts on the vibration transmitting member main body 66; and the curved portion 52 which is continuous with the first proximal portion 37 and the first distal portion 36 and is bent in the direction approaching the vibration transmitting member main body 66.

According to this configuration, the cover 26 abuts on the vibration transmitting member 21 only at the first distal portion 36. Thus, it is possible to prevent as much as possible the conduction of heat of the vibration transmitting member 21 side to the cover 26. Thereby, the temperature of the cover 26 does not rise, and, even if the cover 26 comes in contact with body tissue existing near the region of the treated target, it is possible to prevent the body tissue from being adversely affected.

Third Embodiment

Figure 7:
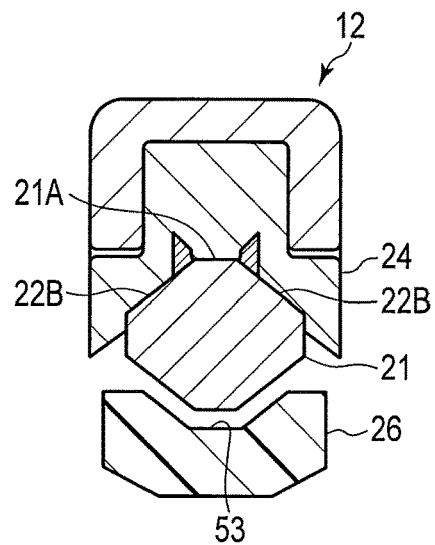
FIG. 7 illustrates a medical device of a third embodiment, FIG. 7 being a cross-sectional view illustrating a cross section of the vibration transmitting member, jaw and cover at a position corresponding to a position of line F7-F7 in FIG. 5.

Referring to FIG. 7, a medical device 11 of a third embodiment will be described. The medical device 11 of the third embodiment differs from that of the first embodiment in that the shape of the cover 26 is different. However, the other parts are common to the first embodiment. Thus, the different part from the first embodiment will mainly be described, and an illustration or description of the parts common to the first embodiment is omitted.

The cover 26 includes a first distal portion 36 which is located on the distal side in the longitudinal direction C of the vibration transmitting member 21, a first proximal portion 37 which is located on the opposite side to the first distal portion 36, and a recess portion 53 which is provided on a surface facing the vibration transmitting member main body 66. The cover 26 is formed of, for example, a synthetic resin material in a tongue shape. The cover 26 covers that side of the vibration transmitting member main body 66, which is opposite to the side thereof facing the jaw 24. The cover 26 is formed of a material which has heat resistance and adiathermancy, and has a lower thermal conductivity than metals or the like.

The recess portion 53 is formed to be recessed in accordance with the shape of the vibration transmitting member main body 66. A part of the vibration transmitting member main body 66 is disposed in the inside of the recess portion 53. A small gap is provided between the vibration transmitting member main body 66 and the cover 26. The cover 26 is disposed closer to the vibration transmitting member main body 66 than in the first embodiment.

Referring to FIG. 7, the function of the medical device 11 of the present embodiment will be described. Before treating body tissue that is a treated target by using the medical device 11 of the present embodiment, the surgeon secures a path (port) for accessing the treated target, by using a cylindrical guide, such as a trocar, which can penetrate a patient's skin or the like.

The surgeon moves the jaw 24 from the spaced position 48 to the abutted position 47. In this state, the vibration transmitting member main body 66 and jaw 24 are inserted into the trocar. At this time, since the cover 26 is disposed near the vibration transmitting member main body 66, when the resistance force acts on the first distal portion 36 of the cover 26, this resistance force can also be received by the vibration transmitting member 21 side. Thus, sharp bending or the like does not occur in the cover 26. Therefore, the vibration transmitting member 21 and jaw 24 can smoothly reach the region of the treated target.

In the region of the treated target, the surgeon can clamp the body tissue between the vibration transmitting member main body 66 and jaw 24. Furthermore, by operating the energy operation input button 27 in this state, the surgeon can perform, like the first embodiment, the coagulation and incision or only the coagulation of the body tissue and blood vessel.

According to the third embodiment, the cover 26 includes the recess portion 53 which is recessed in accordance with the shape of the vibration transmitting member main body 66. According to this configuration, the cover 26 can be disposed as close as possible to the vibration transmitting member main body 66. Thus, the gap between the vibration transmitting member main body 66 and cover 26 is decreased, and, when the body tissue is coagulated and incised, it is possible to prevent as much as possible the removed piece of body tissue from entering between the vibration transmitting member main body 66 and cover 26. Besides, if the cover 26 can be disposed close to the vibration transmitting member main body 66, the cover 26 does not become a hindrance at a time of treatment, and the work efficiency of the surgeon can be improved.

Fourth Embodiment

Figure 8:
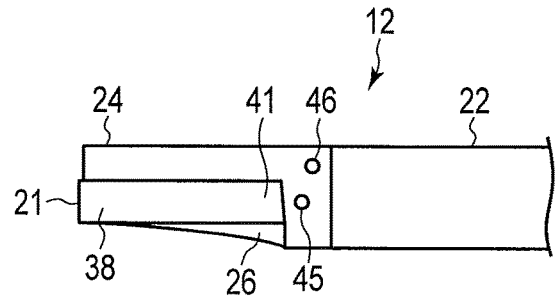
FIG. 8 is a side view illustrating a vibration transmitting member, a jaw and a cover of a medical device of a fourth embodiment.

Referring to FIG. 8, a medical device 11 of a fourth embodiment will be described. The medical device 11 of the fourth embodiment differs from that of the first embodiment in that the shape, material, etc. of the cover 26 are different. However, the other parts are common to the first embodiment. Thus, the different parts from the first embodiment will mainly be described, and an illustration or description of the parts common to the first embodiment is omitted.

The cover 26 is provided in close contact with that surface of the vibration transmitting member main body 66, which is located on the side opposite to the surface thereof facing the jaw 24. The cover 26 is formed of, for example, an elastic material (thin-film material). The elastic material is formed of, for example, a synthetic resin material with elasticity like rubber. When the vibration transmitting member 21 bends, the cover 26 can bend in a manner to follow the bending of the vibration transmitting member main body 66. The thickness of the cover 26 is substantially zero on the second distal portion 38 side of the vibration transmitting member main body 66, and the thickness of the cover 26 gradually increases toward the second proximal portion 41 of the vibration transmitting member main body 66.

Referring to FIG. 8, the function of the medical device 11 of the present embodiment will be described. Before treating body tissue that is a treated target by using the medical device 11 of the present embodiment, the surgeon secures a path (port) for accessing the treated target, by using a cylindrical guide, such as a trocar, which can penetrate a patient's skin or the like.

The surgeon moves the jaw 24 from the spaced position 48 to the abutted position 47. In this state, the vibration transmitting member 21 and jaw 24 are inserted into the trocar. At this time, since the cover 26 is put in close contact with the vibration transmitting member main body 66, the resistance force acting on the cover 26 can be received by the vibration transmitting member 21. Thus, peeling or the like does not occur in the cover 26. Therefore, the vibration transmitting member main body 66 and jaw 24 can smoothly reach the region of the treated target.

In the region of the treated target, the surgeon can clamp the body tissue between the vibration transmitting member main body 66 and jaw 24. Furthermore, by operating the energy operation input button 27 in this state, the surgeon can perform, like the first embodiment, the coagulation and incision or only the coagulation of the body tissue and blood vessel.

According to the present embodiment, the cover 26 is provided in close contact with the vibration transmitting member main body 66, and is formed of an elastic material which can bend in a manner to follow the vibration transmitting member main body 66 when the vibration transmitting member 21 is bent.

According to this configuration, no gap is provided between the cover 26 and the vibration transmitting member 21. When body tissue is coagulated and incised, it is possible to exactly prevent a removed piece of body tissue from entering between the vibration transmitting member 21 and cover 26. In addition, since the cover 26 is put in close contact with the vibration transmitting member 21, the cover 26 does not become a hindrance at a time of treatment, and the work efficiency of the surgeon can be improved. Moreover, when the vibration transmitting member 21 and jaw 24 are inserted into the region of the treated target, the pressure acting on the cover 26 can be received by the vibration transmitting member 21, and it is thus possible to prevent the cover 26 from being sharply bent or dropped at the time of insertion.

Fifth Embodiment

Referring to FIG. 9 and FIG. 10, a medical device 11 of a fifth embodiment will be described. The medical device 11 of the fifth embodiment differs from that of the first embodiment in that the shape of the cover 26 is different. However, the other parts are common to the first embodiment. Thus, the different part from the first embodiment will mainly be described, and an illustration or description of the parts common to the first embodiment is omitted.

The cover 26 is provided along the direction C in which the vibration transmitting member 21 extends. The cover 26 includes a first distal portion 36 which is located on the distal side in the longitudinal direction C of the vibration transmitting member 21, and a first proximal portion 37 which is located on the opposite side to the first distal portion 36 in the longitudinal direction C. The cover 26 is formed, for example, in a tongue shape. A small gap is provided between the cover 26 and the vibration transmitting member main body 66. The cover 26 covers that side of the vibration transmitting member main body 66, which is opposite to the side thereof facing the jaw 24. The cover 26 is formed of a material, such as a synthetic resin material, which has heat resistance and adiathermancy, and has a lower thermal conductivity than metals or the like.

The cover 26 exposes the second distal portion 38 of the vibration transmitting member 21 to the outside, and covers the position deviating from the second distal portion 38. Thus, in the present embodiment, as illustrated in FIG. 9, a height dimension h of the vibration transmitting member main body 66 and jaw 24 in a direction crossing the longitudinal direction C can be decreased. In addition, as illustrated in FIG. 10, a width dimension D1 of the first distal portion 36 in a direction crossing the longitudinal direction C is less than a width dimension D2 of the first proximal portion 37 in the direction crossing the longitudinal direction C.

Referring to FIG. 9, the function of the medical device 11 of the present embodiment will be described. Before treating body tissue that is a treated target by using the medical device 11 of the present embodiment, the surgeon secures a path (port) for accessing the treated target, by using a cylindrical guide, such as a trocar, which can penetrate a patient's skin or the like.

The surgeon moves the jaw 24 from the spaced position 48 to the abutted position 47. In this state, the vibration transmitting member main body 66 and jaw 24 are inserted into the trocar. At this time, since the cover 26 is disposed near the vibration transmitting member main body 66, when the resistance force acts on the first distal portion 36 of the cover 26, this resistance force can also be received by the vibration transmitting member 21 side. Thus, sharp bending or the like does not occur in the cover 26. Therefore, the vibration transmitting member main body 66 and jaw 24 can smoothly reach the region of the treated target.

In the region of the treated target, the surgeon can clamp the body tissue between the vibration transmitting member main body 66 and jaw 24. At this time, since the height dimension h of the vibration transmitting member main body 66 and jaw 24 and the width dimension D1 of the first distal portion 36 of the cover 26 are decreased, the vibration transmitting member main body 66 and jaw 24 can be inserted into even a narrow location in the body. Furthermore, by operating the energy operation input button 27 in this state, the surgeon can perform, like the first embodiment, the coagulation and incision or only the coagulation of the body tissue and blood vessel.

According to the present embodiment, the cover 26 covers the vibration transmitting member main body 66 at the position deviating from the second distal portion 38 which is located at the distal end of the vibration transmitting member main body 66. According to this configuration, in the vicinity of the second distal portion 38 of the vibration transmitting member main body 66, the height dimension h of the vibration transmitting member main body 66 and jaw 24 can be decreased. Thus, the accessibility to the region of the treated target can be enhanced, the convenience for the surgeon can be improved, and the time of surgery can be shortened.

The cover 26 includes the first proximal portion 37, and the first distal portion 36 which is formed to have a less width than the first proximal portion 37 in the direction crossing the longitudinal direction C of the vibration transmitting member 21. According to this configuration, since the width dimension D1 of the first distal portion 36 of the cover 26 can be made less than the width dimension D2 of the first proximal portion 37, the accessibility to the region of the treated target can be enhanced, the convenience for the surgeon can be improved, and the time of surgery can be shortened.

Sixth Embodiment

Referring to FIG. 11, a medical device of a sixth embodiment will be described. A medical device 11 of the sixth embodiment differs from that of the first embodiment in that the shapes of the jaw 24 and cover 26 are different from those in the first embodiment. However, the other parts are common to the first embodiment. Thus, the different parts from the first embodiment will mainly be described, and an illustration or description of the parts common to the first embodiment is omitted.

A width dimension W2 of the jaw 24 in a direction crossing the longitudinal direction C is set to be greater than a width dimension W1 of the vibration transmitting member main body 66 in the direction crossing the longitudinal direction C.

The cover 26 covers that side of the vibration transmitting member main body 66, which is opposite to the side thereof facing the jaw 24. The cover 26 is formed of a material, such as a synthetic resin material, which has heat resistance and adiathermancy, and has a lower thermal conductivity than metals or the like. A width dimension W3 of the cover in the direction crossing the longitudinal direction C is set to be greater than the width dimension W1 of the vibration transmitting member 21 in the direction crossing the longitudinal direction C. Thus, according to the jaw 24 and cover 26 of the present embodiment, it is possible to protect the vibration transmitting member main body 66 by covering, without discontinuity, the periphery (entire periphery) of the vibration transmitting member main body 66 whose temperature rises to 200° C. or above.

Referring to FIG. 11, the function of the medical device 11 of the present embodiment will be described. Before treating body tissue that is a treated target by using the medical device 11 of the present embodiment, the surgeon secures a path (port) for accessing the treated target, by using a cylindrical guide, such as a trocar, which can penetrate a patient's skin or the like. By the same method as in the first embodiment, the surgeon makes the vibration transmitting member main body 66 and jaw 24 reach the region of the treated target.

In the region of the treated target, the surgeon can clamp the body tissue between the vibration transmitting member main body 66 and jaw 24. Furthermore, by operating the energy operation input button 27 in this state, the surgeon can perform, like the first embodiment, the coagulation and incision or only the coagulation of the body tissue and blood vessel.

In the present embodiment, the entire periphery of the vibration transmitting member main body 66 is protected by the jaw 24 and cover 26. Thus, such a situation does not occur that the vibration transmitting member main body 66 is, when not intended, put in contact with nearby body tissue.

According to this embodiment, the width dimension W1 of the vibration transmitting member main body 66 in the direction crossing the longitudinal direction C of the vibration transmitting member 21 is less than the width dimension W3 of the cover 26 in the direction crossing the longitudinal direction C. According to this configuration, it is possible to cover, without discontinuity, the periphery of the vibration transmitting member main body 66. Therefore, it is possible to prevent such a situation that the vibration transmitting member main body 66 at high temperatures is put in contact with body tissue existing near the treated target, when not intended by the surgeon. Thereby, the convenience for the surgeon can be enhanced, and the load on the patient can be reduced.

Seventh Embodiment

Figure 12:
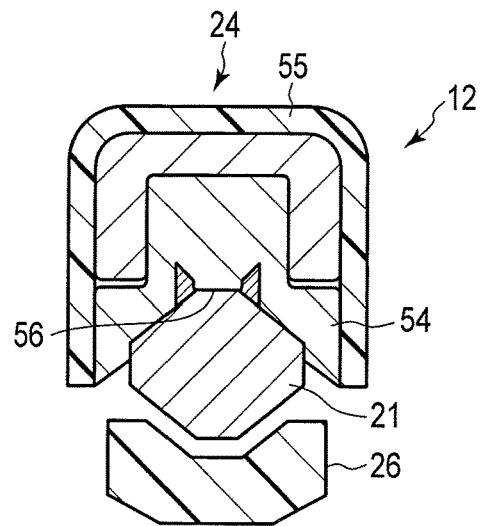
FIG. 12 illustrates a medical device of a seventh embodiment, FIG. 12 being a cross-sectional view illustrating a cross section of the vibration transmitting member, jaw, cover, and a second cover at a position corresponding to a position of line F7-F7 in FIG. 5.

Referring to FIG. 12, a medical device of a seventh embodiment will be described. A medical device 11 of the seventh embodiment differs from that of the first embodiment in that the shape of the jaw 24 is different. However, the other parts are common to the first embodiment. Thus, the different part from the first embodiment will mainly be described, and an illustration or description of the parts common to the first embodiment is omitted.

The jaw 24 includes a jaw main body 54 having a surface opposed to the vibration transmitting member main body 66, and a second cover 55 which covers the jaw main body 54. The jaw main body 54 is formed in a plate shape having a recess portion 53 for storing the vibration transmitting member main body 66, such that the jaw main body 54 is engaged with the vibration transmitting member main body 66 having the octagonal cross section. The jaw main body 54 is formed of a metallic material (e.g. stainless steel, etc.) in which a copper alloy is fixed as an electrode. The second cover 55 covers that part of the jaw main body 54, which excludes the surface (opposed surface 56) opposed to the vibration transmitting member main body 66. The second cover 55 is formed of a material, such as a synthetic resin material, which has a high adiathermancy, and has a lower thermal conductivity than metals. In the meantime, although the temperature of the vibration transmitting member main body 66 exceeds 200° C. during an ultrasonic treatment, several tens of percent of the heat generated by the vibration transmitting member main body 66 is conducted to the jaw 24 side, and the temperature of the jaw 24 also becomes high.

Referring to FIG. 12, the function of the medical device 11 of the present embodiment will be described. Before treating body tissue that is a treated target by using the medical device 11 of the present embodiment, the surgeon makes the vibration transmitting member main body 66 and jaw 24 reach the region of the treated target in the patient's body by the same method as in the first embodiment.

In the region of the treated target, the surgeon can clamp the body tissue between the vibration transmitting member main body 66 and jaw 24. Furthermore, by operating the energy operation input button 27 in this state, the surgeon can perform, like the first embodiment, the coagulation and incision or only the coagulation of the body tissue and blood vessel. In the present embodiment, that part of the metallic jaw 24, which excludes the surface opposed to the vibration transmitting member main body 66, is protected by the second cover 55. Thus, such a situation does not occur that the jaw 24 at high temperatures is, when not intended, put in contact with nearby body tissue.

According to the present embodiment, the second cover 55 is provided which covers that side of the jaw 24, which is opposite to the opposed surface 56 facing the vibration transmitting member main body 66. According to this configuration, it is possible to prevent such a situation that the jaw 24 at high temperatures is put in contact with body tissue existing near the treated target, when not intended by the surgeon. Thereby, the convenience for the surgeon can be enhanced, and the load on the patient can be reduced.

Eighth Embodiment

Figure 13:
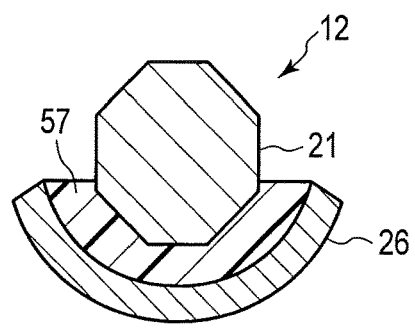
FIG. 13 illustrates a medical device of an eighth embodiment, FIG. 13 being a cross-sectional view illustrating a cross section of the vibration transmitting member, cover, and a filler at a position corresponding to a position of line F7-F7 in FIG. 5.

Referring to FIG. 13, a medical device of an eighth embodiment will be described. A medical device 11 of the eighth embodiment differs from that of the first embodiment in that a filler 57 is interposed between the vibration transmitting member main body 66 and the cover 26. However, the other parts are common to the first embodiment. Thus, the different part from the first embodiment will mainly be described, and an illustration or description of the parts common to the first embodiment is omitted.

As illustrated in FIG. 1, FIG. 3, FIG. 13, etc., the handpiece 12 includes a held section 15 which constitutes an outer shell; a stationary handle 16 which is fixedly provided on the held section 15; a movable handle 17 which is rotatable relative to the held section 15; a vibration generator 18 (transducer) which is stored in the held section 15; a rod-shaped vibration transmitting member 21 which is connected to the vibration generator 18; a cylindrical sheath 22 which covers the periphery of the vibration transmitting member 21 and protects the vibration transmitting member 21; a knob 23 (rotary knob) which is fixed to the sheath 22; a jaw 24 which is provided to be rotatable relative to the vibration transmitting member 21 and sheath 22; a driving pipe 25 which is provided in the inside of the sheath 22 and is advanced and retreated when the jaw 24 is opened and closed; a cover 26 which is provided in such a position that the vibration transmitting member main body 66 is interposed between the cover 26 and the jaw 24; and a filler 57 which is interposed between the vibration transmitting member main body 66 and the cover 26.

The filler 57 is formed of a material, such as a synthetic resin material, which has heat resistance and adiathermancy, and has a relatively low thermal conductivity. The filler 57 may be formed of, for example, rubber or an adhesive. In addition, the filler 57 may be, for example, a material which is denatured by heat, such as a wax. Besides, the filler 57 may be a gel with thixotropy.

Referring to FIG. 13, the function of the medical device 11 of the present embodiment will be described. Before treating body tissue that is a treated target by using the medical device 11 of the present embodiment, the surgeon makes the vibration transmitting member main body 66 and jaw 24 reach the region of the treated target in the patient's body by the same method as in the first embodiment.

In the region of the treated target, the surgeon can clamp the body tissue between the vibration transmitting member main body 66 and jaw 24. Furthermore, by operating the energy operation input button 27 in this state, the surgeon can perform, like the first embodiment, the coagulation and incision or only the coagulation of the body tissue and blood vessel. In the present embodiment, since the filler 57 is interposed between the vibration transmitting member 21 and the cover 26, a piece of body tissue, coagulated blood, etc., which occurred in the coagulation and incision, are prevented from entering between the vibration transmitting member main body 66 and the cover 26.

According to the present embodiment, the filler 57 is interposed between the vibration transmitting member main body 66 and the jaw 24. According to this configuration, a piece of body tissue, coagulated blood, etc. do not enter between the vibration transmitting member main body 66 and the cover 26, and it is possible to prevent such a piece of body tissue, etc. from being burnt and adhering to the vibration transmitting member 21, and being caught (coagulated) between the vibration transmitting member main body 66 and the cover 26.

Ninth Embodiment

Figure 14:
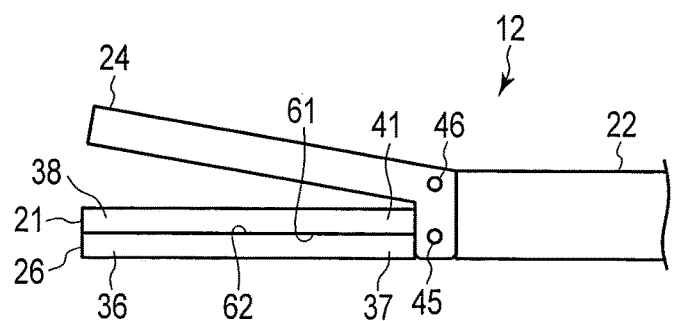
FIG. 14 is a side view illustrating a vibration transmitting member, a jaw and a cover of a medical device of a ninth embodiment.

Referring to FIG. 14, a medical device of a ninth embodiment will be described. A medical device 11 of the ninth embodiment differs from that of the first embodiment in that the material of the cover 26 is different. However, the other parts are common to the first embodiment. Thus, the different part from the first embodiment will mainly be described, and an illustration or description of the parts common to the first embodiment is omitted.

The vibration transmitting member main body 66 includes a first surface 61 which is opposed to the cover 26.

The cover 26 is formed of a fluororesin such as polytetrafluoroethylene (tetrafluororesin). Thus, in the present embodiment, the heat resistance and sliding properties of the surface of the cover 26 are improved, and a low frictional property of the cover 26 is realized. The other structure of the cover 26 is the same as in the first embodiment. The cover 26 includes a second surface 62 which is opposed to the vibration transmitting member main body 66.

Referring to FIG. 14, the function of the medical device 11 of the present embodiment will be described. Before treating body tissue that is a treated target by using the medical device 11 of the present embodiment, the surgeon makes the vibration transmitting member main body 66 and jaw 24 reach the region of the treated target in the patient's body by the same method as in the first embodiment.

In addition, like the first embodiment, in the region of the treated target, the surgeon can clamp the body tissue between the vibration transmitting member main body 66 and jaw 24, and can perform, by operating the energy operation input button 27, the coagulation and incision or only the coagulation of the body tissue and blood vessel. In the present embodiment, the cover 26 has the low frictional property. Thus, even if the vibration transmitting member main body 66, which is performing ultrasonic vibration, comes in contact with the cover 26, a temperature rise of the cover 26 due to frictional heat can be prevented as much as possible.

According to the present embodiment, the medical device 11 includes the first surface 61 which is provided on the vibration transmitting member 21 side and is opposed to the cover 26, and the second surface 62 which is provided on the cover 26 side and is opposed to the vibration transmitting member main body 66. At least one of the first surface 61 and second surface 62 has low frictional properties.

According to this configuration, even if the vibration transmitting member main body 66, which is performing ultrasonic vibration, comes in contact with the cover 26, the frictional heat occurring between the vibration transmitting member main body 66 and the cover 26 can be reduced, and a rise in temperature of the cover 26 can be prevented. Thereby, even if the surgeon unintentionally puts the cover 26 in contact with body tissue existing near the treated target, it is possible to prevent the nearby body tissue from being adversely affected by heat.

(First Modification)

Figure 15:
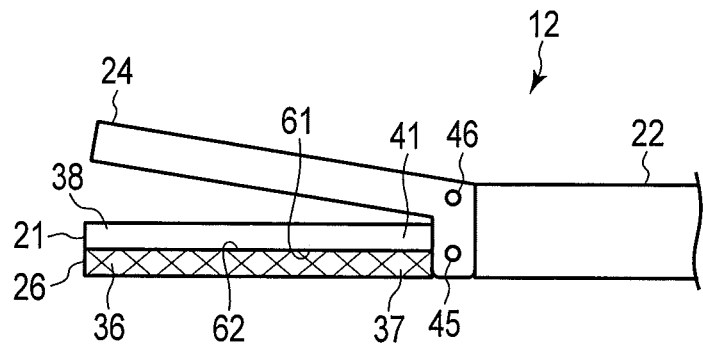
FIG. 15 is a side view illustrating a vibration transmitting member, a jaw and a cover of a medical device of a first modification of the ninth embodiment.

Referring to FIG. 15, a first modification of the medical device 11 of the ninth embodiment will be described. The medical device 11 of the first modification differs from that of the ninth embodiment in that the structures of the vibration transmitting member main body 66 and cover 26 are different. However, the other parts are common to the ninth embodiment. Thus, an illustration or description of the parts common to the ninth embodiment is omitted.

The cover 26 (a base portion of the cover 26) is formed of, for example, a synthetic resin material. The cover 26 includes a surface (second surface 62) which is opposed to the vibration transmitting member main body 66. A coating by a thin film of a fluororesin, such as polytetrafluoroethylene (tetrafluororesin), is formed on the entire surface of the cover 26, or on at least the second surface 62 of the cover 26. The other structure of the cover 26 is the same as in the ninth embodiment. According to the medical device 11 of the present modification, the same function as in the ninth embodiment can be exhibited.

According to the present modification, at least one of the first surface 61 on the vibration transmitting member 21 side and the second surface 62 on the cover 26 side has low frictional properties. According to this configuration, the frictional heat, which occurs when the vibration transmitting member main body 66 that is performing ultrasonic vibration comes in contact with the cover 26, can be reduced, and a rise in temperature of the cover 26 can be prevented. Thereby, even if the surgeon unintentionally puts the cover 26 in contact with body tissue existing near the treated target, it is possible to prevent the nearly body tissue from being adversely affected by heat.

(Second Modification)

Figure 16:
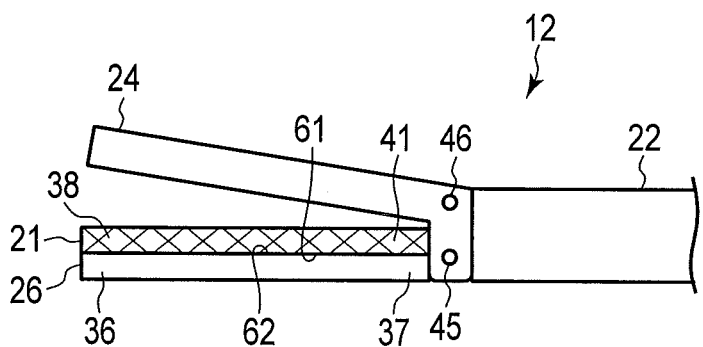
FIG. 16 is a side view illustrating a vibration transmitting member, a jaw and a cover of a medical device of a second modification of the ninth embodiment.

Referring to FIG. 16, a second modification of the medical device of the ninth embodiment will be described. The medical device 11 of the second modification differs from that of the ninth embodiment in that the structure of the cover 26 is different. However, the other parts are common to the ninth embodiment. Thus, an illustration or description of the parts common to the ninth embodiment is omitted.

The cover 26 has the same structure as in the first embodiment.

The vibration transmitting member 21 is formed of, for example, a biocompatible metallic material (e.g. a titanium alloy, etc.) in a rod shape. The vibration transmitting member 21 includes a second distal portion 38 which is located on the distal side in the longitudinal direction C thereof, and a second proximal portion 41 which is located on a side (proximal side) opposite to the second distal portion 38.

The vibration transmitting member main body 66 includes a first surface 61 which is opposed to the cover 26. A coating by a thin film of a fluororesin, such as polytetrafluoroethylene (tetrafluororesin), is formed on the entire surface of the vibration transmitting member main body 66, or on at least the first surface 61 of the vibration transmitting member main body 66. The other structure of the vibration transmitting member main body 66 is the same as in the ninth embodiment. According to the medical device 11 of the present modification, the same function as in the ninth embodiment can be exhibited.

According to the present modification, at least one of the first surface 61 on the vibration transmitting member 21 side and the second surface 62 on the cover 26 side has low frictional properties. According to this configuration, the frictional heat, which occurs when the vibration transmitting member main body 66 that is performing ultrasonic vibration comes in contact with the cover 26, can be reduced, and a rise in temperature of the cover 26 can be prevented. Thereby, even if the surgeon unintentionally puts the cover 26 in contact with body tissue existing near the treated target, it is possible to prevent the nearby body tissue from being adversely affected by heat.

Tenth Embodiment

Figure 17:
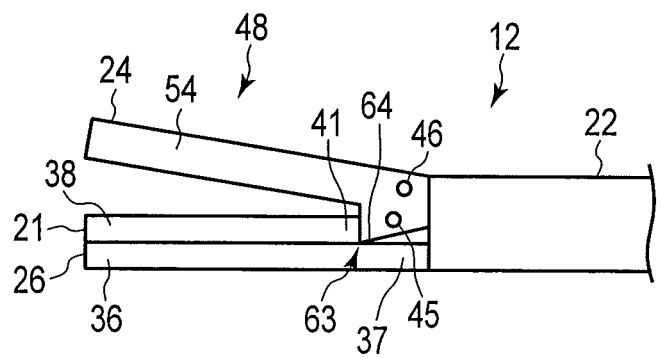
FIG. 17 is a side view illustrating a vibration transmitting member, a jaw and a cover of a medical device of a tenth embodiment.
Figure 18:
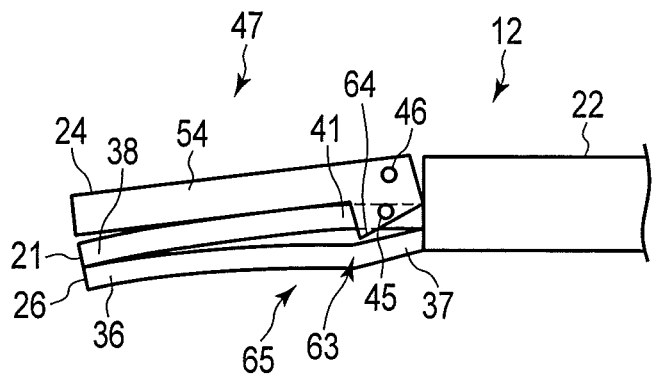
FIG. 18 is a side view illustrating a state in which the jaw shown in FIG. 17 is moved to an abutted position.

Referring to FIG. 17 and FIG. 18, a medical device of a tenth embodiment will be described. A medical device 11 of the tenth embodiment differs from that of the first embodiment in that the jaw 24 includes an evacuation mechanism 63 for evacuating the cover 26. However, the other parts are common to the first embodiment. Thus, the different part from the first embodiment will mainly be described, and an illustration or description of the parts common to the first embodiment is omitted.

The jaw 24 includes the jaw main body 54 which is movable between the abutted position 47 where the jaw 24 abuts on the vibration transmitting member main body 66, and the spaced position 48 where the jaw 24 is spaced apart from the vibration transmitting member 21; and an evacuation mechanism 63 which is formed in a manner to project from the jaw main body 54. The jaw 24 is supported by the support pin 45 which is fixed to the distal portion of the sheath 22, and is attached so as to be rotatable about the support pin 45. By operating the movable handle 17, the jaw 24 can be moved between the abutted position 47 where the jaw 24 can abut on the vibration transmitting member main body 66 and can grasp body tissue, and the spaced position 48 where the jaw 24 is spaced apart from the vibration transmitting member main body 66.

The jaw main body 54 is formed in a plate shape having a recess portion for storing the vibration transmitting member main body 66, such that the jaw main body 54 is engaged with the vibration transmitting member main body 66 having the octagonal cross section. The evacuation mechanism 63 is provided to be integral with the jaw main body 54. The evacuation mechanism 63 includes an abutment portion 64 which projects so as to be able to push the cover 26 in a direction away from the vibration transmitting member main body 66. The jaw 24 is formed of a metallic material such as a stainless steel alloy.

Referring to FIG. 17 and FIG. 18, the function of the medical device 11 of the present embodiment will be described. Before treating body tissue that is a treated target by using the medical device 11 of the present embodiment, the surgeon secures a path (port) for accessing the treated target, by using a cylindrical guide, such as a trocar, which can penetrate a patient's skin or the like.

The surgeon moves the jaw 24 from the spaced position 48 illustrated in FIG. 17 to the abutted position 47 illustrated in FIG. 18. Thereby, by the urging force of the jaw 24, the vibration transmitting member main body 66 bends toward the cover 26, and the second distal portion 38 of the vibration transmitting member main body 66 abuts on the first distal portion 36 of the cover 26. In this state, the gap between the second distal portion 38 of the vibration transmitting member main body 66 and the first distal portion 36 of the cover 26 is closed. On the other hand, in the abutted position 47, the evacuation mechanism 63 operates to push the cover 26 in the vicinity of the first proximal portion 37 in a direction (to a separate position 65) away from the vibration transmitting member 21. In this state, the vibration transmitting member main body 66 and jaw 24 are inserted into the trocar. Thereby, the vibration transmitting member main body 66 and jaw 24 can smoothly reach the region of the treated target.

In the region of the treated target, by moving the jaw 24 to the abutted position 47, the surgeon can clamp the body tissue between the vibration transmitting member main body 66 and jaw 24. Furthermore, if the surgeon operates the energy operation input button 27, the surgeon can apply energy to the clamped body tissue. If the second energy operation input button 27B which corresponds to the coagulation/incision mode is operated, the vibration transmitting member main body 66 performs ultrasonic vibration, and applies thermal energy by frictional movement to the body tissue. Thereby, the body tissue and blood vessel can be incised between the vibration transmitting member main body 66 and the jaw 24. At the same time, a high-frequency current is passed through the body tissue between the vibration transmitting member main body 66 serving as the electrode and the jaw 24, and electric energy can be applied to the body tissue. Thereby, the body tissue and blood vessel can be coagulated.

At this time, the cover 26 is pushed in the direction away from the vibration transmitting member main body 66 by the evacuation mechanism 63, and the cover 26 abuts on the vibration transmitting member main body 66 only at the first distal portion 36. Thus, the amount of heat, which is conducted from the vibration transmitting member main body 66 to the cover 26, can be decreased.

In addition, in the state in which the body tissue is clamped between the vibration transmitting member main body 66 and the jaw 24, if the surgeon operates the first energy operation input button 27A, the high-frequency current is passed through the body tissue between the second surface 62 of the vibration transmitting member 21 serving as the electrode and the jaw 24, and electric energy can be applied to the body tissue. Thereby, only the coagulation of the body tissue can be performed.

According to the present embodiment, the medical device 11 includes the evacuation mechanism 63 which evacuates the cover 26 to the separate position 65 spaced apart from the vibration transmitting member 21, when the jaw 24 is moved to the abutted position 47. According to this configuration, even when the vibration transmitting member main body 66 vibrates and has high temperatures in the abutted position 47, the contact area between the vibration transmitting member main body 66 and the cover 26 can be minimized, and the amount of heat, which is conducted from the vibration transmitting member main body 66 to the cover 26, can be decreased. Thereby, the cover 26 is prevented from having high temperatures, and, even if the cover 26 comes in contact with body tissue existing near the region of the treated target during the treatment, it is possible to prevent the body tissue from being adversely affected by heat.

Eleventh Embodiment

Figure 19:
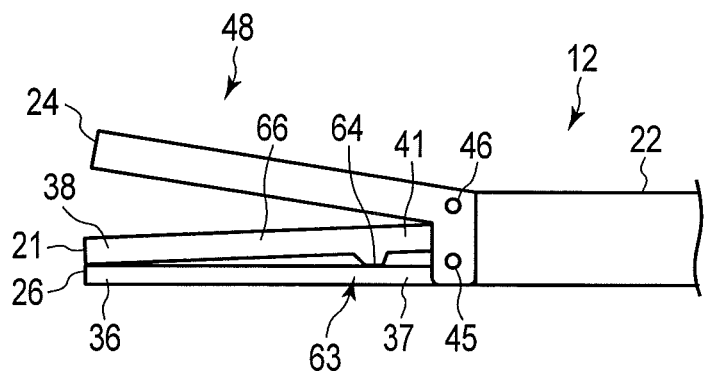
FIG. 19 is a side view illustrating a vibration transmitting member, a jaw and a cover of a medical device of an eleventh embodiment.
Figure 20:
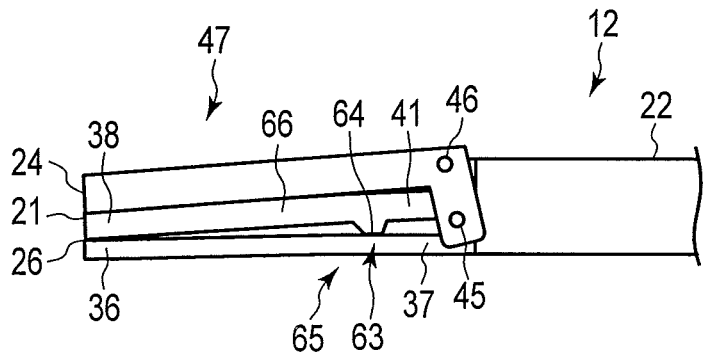
FIG. 20 is a side view illustrating a state in which the jaw shown in FIG. 19 is moved to an abutted position.

Referring to FIG. 19 and FIG. 20, a medical device 11 of an eleventh embodiment will be described. The medical device 11 of the eleventh embodiment differs from that of the first embodiment in that the vibration transmitting member 21 includes an evacuation mechanism 63 for evacuating the cover 26. However, the other parts are common to the first embodiment. Thus, the different part from the first embodiment will mainly be described, and an illustration or description of the parts common to the first embodiment is omitted.

The vibration transmitting member 21 is formed of, for example, a biocompatible metallic material (e.g. a titanium alloy, etc.) in a rod shape. A vibration transmitting member main body 66 (to be described later) of the vibration transmitting member 21 includes a second distal portion 38 which is located on the distal side in the longitudinal direction C thereof, and a second proximal portion 41 which is located on a side (proximal side) opposite to the second distal portion 38.

The vibration transmitting member 21 includes the vibration transmitting member main body 66 having, for example, a polygonal cross-sectional shape (e.g. an octagonal cross-sectional shape in the present embodiment), and an evacuation mechanism 63 which is provided in a manner to project from the vibration transmitting member main body 66. The evacuation mechanism 63 is provided to be integral with the vibration transmitting member main body 66. The evacuation mechanism 63 includes an abutment portion 64 which projects so as to be able to push the cover 26 in a direction away from the vibration transmitting member 21.

Referring to FIG. 19 and FIG. 20, the function of the medical device 11 of the present embodiment will be described. Before treating body tissue that is a treated target by using the medical device 11 of the present embodiment, the surgeon secures a path (port) for accessing the treated target, by using a cylindrical guide, such as a trocar, which can penetrate a patient's skin or the like.

The surgeon moves the jaw 24 from the spaced position 48 illustrated in FIG. 19 to the abutted position 47 illustrated in FIG. 20. Thereby, by the urging force of the jaw 24, the vibration transmitting member main body 66 bends toward the cover 26, and the second distal portion 38 of the vibration transmitting member main body 66 abuts on the first distal portion 36 of the cover 26. In this state, the gap between the second distal portion 38 of the vibration transmitting member main body 66 and the first distal portion 36 of the cover 26 is closed. On the other hand, in the abutted position 47, the evacuation mechanism 63 operates to push the cover 26 in the vicinity of the second proximal portion 41 of the vibration transmitting member main body 66 in a direction (to a separate position 65) away from the vibration transmitting member main body 66. In this state, the vibration transmitting member main body 66 and jaw 24 are inserted into the trocar. Thereby, the vibration transmitting member main body 66 and jaw 24 can smoothly reach the region of the treated target.

In the region of the treated target, by moving the jaw 24 to the abutted position 47, the surgeon can clamp the body tissue between the vibration transmitting member main body 66 and jaw 24. Furthermore, if the surgeon operates the energy operation input button 27, the surgeon can apply energy to the clamped body tissue. If the second energy operation input button 27B which corresponds to the coagulation/incision mode is operated, the vibration transmitting member 21 performs ultrasonic vibration, and applies thermal energy by frictional movement to the body tissue. Thereby, the body tissue and blood vessel can be incised between the first surface 61 of the vibration transmitting member main body 66 and the jaw 24. At the same time, a high-frequency current is passed through the body tissue between the second surface 62 of the vibration transmitting member main body 66 serving as the electrode and the jaw 24, and electric energy can be applied to the body tissue. Thereby, the body tissue and blood vessel can be coagulated.

At this time, the cover 26 is pushed in the direction away from the vibration transmitting member main body 66 by the evacuation mechanism 63, and the cover 26 abuts on the vibration transmitting member main body 66 only at the first distal portion 36. Thus, the amount of heat, which is conducted from the vibration transmitting member main body 66 to the cover 26, can be decreased.

In addition, in the state in which the body tissue is clamped between the vibration transmitting member main body 66 and the jaw 24, if the surgeon operates the first energy operation input button 27A, the high-frequency current is passed through the body tissue between the vibration transmitting member 21 serving as the electrode and the jaw 24, and electric energy can be applied to the body tissue. Thereby, only the coagulation of the body tissue can be performed.

According to the present embodiment, the medical device 11 includes the evacuation mechanism 63 which evacuates the cover 26 to the separate position 65 spaced apart from the vibration transmitting member main body 66, when the jaw 24 is moved to the abutted position 47. According to this configuration, even when the vibration transmitting member main body 66 vibrates and has high temperatures in the abutted position 47, the contact area between the vibration transmitting member main body 66 and the cover 26 can be minimized, and the amount of heat, which is conducted from the vibration transmitting member main body 66 to the cover 26, can be decreased. Thereby, the cover 26 is prevented from having high temperatures, and, even if the cover 26 comes in contact with body tissue existing near the region of the treated target during the treatment, it is possible to prevent the body tissue from being adversely affected by heat.

Twelfth Embodiment

Referring to FIG. 21 and FIG. 22, a medical device 11 of a twelfth embodiment will be described. The medical device 11 of the twelfth embodiment differs from that of the first embodiment in that the driving pipe 25 constitutes an evacuation mechanism 63 for evacuating the cover 26. However, the other parts are common to the first embodiment. Thus, the different part from the first embodiment will mainly be described, and an illustration or description of the parts common to the first embodiment is omitted.

The driving pipe 25 is provided such that the driving pipe 25 can advance and retreat in the inside of the sheath 22. The driving pipe 25 includes the driving pin 46 for opening and closing the jaw 24.

The cover 26 includes a shaft portion 67 which is fixed to the sheath 22; a cover main body 68 extending from the shaft portion 67 in a direction along the vibration transmitting member 21; an operation lever 71 extending from the shaft portion 67 toward the driving pin 46; and a notch portion 72 provided in the operation lever 71. The driving pin 46, operation lever 71 and notch portion 72 constitute the evacuation mechanism 63 for evacuating the cover 26 when the jaw 24 is moved to the abutted position 47.

Referring to FIG. 21 and FIG. 22, the function of the medical device 11 of the present embodiment will be described. Before treating body tissue that is a treated target by using the medical device 11 of the present embodiment, the surgeon makes the vibration transmitting member main body 66 and jaw 24 reach the region of the treated target in the patient's body by the same method as in the first embodiment.

In addition, like the first embodiment, in the region of the treated target, the surgeon can clamp the body tissue between the vibration transmitting member 21 and the jaw 24, and can perform, by operating the energy operation input button 27, the coagulation and incision or only the coagulation of the body tissue and blood vessel. In the present embodiment, if the jaw 24 moves to the abutted position 47, the evacuation mechanism 63, which is constituted by the driving pin 46, operation lever 71 and notch portion 72, operates to rotate the cover 26 (cover main body 68) about the shaft portion 67. Thereby, the cover 26 moves away from the vibration transmitting member main body 66. It is thus possible to prevent the heat of the vibration transmitting member main body 66 from being conducted to the cover 26.

According to the present embodiment, the evacuation mechanism 63 is provided which evacuates the cover 26 to the separate position 65 spaced from the vibration transmitting member main body 66, when the jaw 24 has moved to the abutted position 47. According to this configuration, even when the vibration transmitting member main body 66 vibrates and has high temperatures in the abutted position 47, it is possible to prevent the conduction of heat from the vibration transmitting member main body 66 to the cover 26. Thereby, the cover 26 is prevented from having high temperatures, and, even if the cover 26 comes in contact with body tissue existing near the region of the treated target during the treatment, it is possible to prevent the body tissue from being adversely affected by heat.

13th Embodiment

Referring to FIG. 23, a medical device 11 of a 13th embodiment will be described. The medical device 11 of the 13th embodiment differs from that of the first embodiment in that a channel 73 is provided for passing cooling water through the inside of the cover 26. However, the other parts are common to the first embodiment. Thus, the different part from the first embodiment will mainly be described, and an illustration or description of the parts common to the first embodiment is omitted.

The handpiece 12 includes a held section 15 which constitutes an outer shell; a stationary handle 16 which is fixedly provided on the held section 15; a movable handle 17 which is rotatable relative to the held section 15; a vibration generator 18 (transducer) which is stored in the held section 15; a rod-shaped vibration transmitting member 21 which is connected to the vibration generator 18; a cylindrical sheath 22 which covers the periphery of the vibration transmitting member 21 and protects the vibration transmitting member 21; a knob 23 (rotary knob) which is fixed to the sheath 22; a jaw 24 which is provided to be rotatable relative to the vibration transmitting member 21 and sheath 22; a driving pipe 25 which is provided in the inside of the sheath 22 and is advanced and retreated when the jaw 24 is opened and closed; a cover 26 which is provided in such a position that the vibration transmitting member 21 is interposed between the cover 26 and the jaw 24; a tube 75 for supplying cooling water to a channel main body 74 of the cover 26; and a water supply mechanism 76 which supplies water to the tube 75.

The cover 26 includes the channel main body 74 for passing cooling water in the inside of the cover 26. The channel main body 74 penetrates the cover 26 in the longitudinal direction C of the cover 26, and can discharge the cooling water, which is supplied from an opening on the first proximal portion 37 side, to the outside. The water supply mechanism 76, tube 75 and channel main body 74 constitute the channel 73 for passing a fluid for cooling the cover 26.

The tube 75 is connected to the channel main body 74.

Referring to FIG. 23, the function of the medical device 11 of the present embodiment will be described. Before treating body tissue that is a treated target by using the medical device 11 of the present embodiment, the surgeon makes the vibration transmitting member 21 and jaw 24 reach the region of the treated target in the patient's body by the same method as in the first embodiment.

In addition, like the first embodiment, in the region of the treated target, the surgeon can clamp the body tissue between the vibration transmitting member 21 and the jaw 24, and can perform, by operating the energy operation input button 27, the coagulation and incision or only the coagulation of the body tissue and blood vessel. In the present embodiment, during the treatment, cooling water is constantly fed into the channel main body 74 by the water supply mechanism 76 and the tube 75. Thus, even when the heat from the vibration transmitting member main body 66 is conducted to the cover 26, the heat, together with the cooling water, is discharged to the outside of the cover 26. Thereby, a rise in temperature of the cover 26 is prevented.

According to the present embodiment, the medical device 11 includes the channel 73 which can pass the fluid for cooling the cover 26. According to this configuration, even when the heat from the vibration transmitting member main body 66 is conducted to the cover 26, a rise in temperature of the cover 26 can be prevented, and, even if the cover 26 comes in contact with nearby body tissue during the treatment, it is possible to prevent the body tissue from being adversely affected by heat.

(First Modification)

Referring to FIG. 24, a first modification of the medical device 11 of the 13th embodiment will be described. The medical device of the first modification differs from that of the 13th embodiment in that the structure of the channel 73 for cooling the cover 26 is different. However, the other parts are common to the 13th embodiment. Thus, an illustration or description of the parts common to the 13th embodiment is omitted.

The handpiece 12 includes a held section 15 which constitutes an outer shell; a stationary handle 16 which is fixedly provided on the held section 15; a movable handle 17 which is rotatable relative to the held section 15; a vibration generator 18 (transducer) which is stored in the held section 15; a rod-shaped vibration transmitting member 21 which is connected to the vibration generator 18; a cylindrical sheath 22 which covers the periphery of the vibration transmitting member 21 and protects the vibration transmitting member 21; a knob 23 (rotary knob) which is fixed to the sheath 22; a jaw 24 which is provided to be rotatable relative to the vibration transmitting member 21 and sheath 22; a driving pipe 25 which is provided in the inside of the sheath 22 and is advanced and retreated when the jaw 24 is opened and closed; a cover 26 which is provided in such a position that the vibration transmitting member 21 is interposed between the cover 26 and the jaw 24; a cylindrical "SILGATOR" (silicone jacket irrigator) 77 which surrounds the sheath 22, the vibration transmitting member 21, the jaw 24, and the cover 26; and a water supply mechanism 76 for supplying cooling water to the SILGATOR 77.

The structure other than the cover 26 and SILGATOR 77 is the same as in the 13th embodiment. Unlike the 13th embodiment, the channel main body 74 is not provided in the cover 26. A gap, which is created between the sheath 22, vibration transmitting member 21, jaw 24 and cover 26, on the one hand, and the SILGATOR 77 on the outside of them, on the other hand, constitutes the channel 73 for passing the fluid for cooling the cover 26.

Referring to FIG. 24, the function of the medical device 11 of the present embodiment will be described. Before treating body tissue that is a treated target by using the medical device 11 of the present embodiment, the surgeon makes the vibration transmitting member main body 66 and jaw 24 reach the region of the treated target in the patient's body by the same method as in the first embodiment.

In addition, like the first embodiment, in the region of the treated target, the surgeon can clamp the body tissue between the vibration transmitting member 21 and the jaw 24, and can perform, by operating the energy operation input button 27, the coagulation and incision or only the coagulation of the body tissue and blood vessel. In the present embodiment, during the treatment, cooling water is constantly fed into the SILGATOR 77 by the water supply mechanism 76, and the cooling water is discharged to the outside from the distal end of the SILGATOR 77. Thus, even when the heat from the vibration transmitting member main body 66 is conducted to the cover 26, the heat, together with the cooling water, is discharged to the outside of the cover 26. Thereby, a rise in temperature of the cover 26 is prevented.

According to the present embodiment, a rise in temperature of the cover 26 can be prevented by the configuration in which the fluid for cooling is passed through the channel 73. Even if the cover 26 comes in contact with nearby body tissue during the treatment, it is possible to prevent the body tissue from being adversely affected by heat.

14th Embodiment

Referring to FIG. 25A and FIG. 25B, a medical device of a 14th embodiment will be described. The medical device 11 of the 14th embodiment differs from that of the 13th embodiment in that a water supply conduit 78, in place of the channel 73, is provided in the inside of the cover 26. However, the other parts are common to the 13th embodiment. Thus, the different part from the 13th embodiment will mainly be described, and an illustration or description of the parts common to the 13th embodiment is omitted.

The cover 26 is formed of a material, such as a synthetic resin material, which has heat resistance and adiathermancy, and has a lower thermal conductivity than metals or the like. The cover 26 includes a near-side portion 81 located on a side facing the vibration transmitting member main body 66, and a far-side portion 82 provided on a side opposite to the near-side portion 81. In the far-side portion 82 of the cover 26, the water supply conduit 78 for passing cooling water through the inside is provided. The water supply conduit 78 is provided in the longitudinal direction C of the cover 26. Unlike the 13th embodiment, the opening on the first distal portion 36 side of the water supply conduit 78 is closed. The opening on the first proximal portion 37 side of the water supply conduit 78 is connected to the tube 75. Cooling water can be injected into the inside of the water supply conduit 78.

Referring to FIG. 25A and FIG. 25B, the function of the medical device 11 of the present embodiment will be described. Prior to a treatment, the surgeon can fill the inside of the water supply conduit 78 with cooling water via the tube 75 by using a syringe 83 or the like. In addition, before treating body tissue that is a treated target by using the medical device 11 of the present embodiment, the surgeon makes the vibration transmitting member main body 66 and jaw 24 reach the region of the treated target in the patient's body by the same method as in the first embodiment.

In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel. At this time, if the heat of the vibration transmitting member main body 66 is conducted to the cover 26, a thermal expansion amount increases in the near-side portion 81 of the cover 26. On the other hand, in the far-side portion 82, a temperature rise is decreased by the cooling water filled in the water supply conduit 78, and the thermal expansion amount is suppressed to be small. Thus, as illustrated in FIG. 25B, even when the heat from the vibration transmitting member main body 66 is conducted to the cover 26, the cover 26 bends in a manner to warp in a direction away from the vibration transmitting member main body 66. Thereby, on the first distal portion 36 side, the cover 26 is separated from the vibration transmitting member main body 66, and the temperature of the cover 26 is prevented from further rising.

According to the present embodiment, the cover 26 includes the near-side portion 81 located on the side facing the vibration transmitting member main body 66, and the far-side portion 82 provided on the side opposite to the near-side portion 81 and configured to have a lower thermal expansion amount than the near-side portion 81.

According to this configuration, when a temperature rise occurs in the cover 26 by the heat conducted from the vibration transmitting member main body 66, the cover 26 can be bent in a manner to warp in a direction away from the vibration transmitting member main body 66. Thus, the cover 26 can be separated from the vibration transmitting member main body 66. Thereby, a further temperature rise in the cover 26 can be prevented, and, even if the cover 26, when not intended, comes in contact with nearby body tissue during the treatment, it is possible to prevent the nearby body tissue from being adversely affected by heat.

15th Embodiment

Referring to FIG. 26A and FIG. 26B, a medical device of a 15th embodiment will be described. The medical device 11 of the 15th embodiment differs from that of the 14th embodiment in that the water supply conduit 78 is not provided in the inside of the cover 26. However, the other parts are common to the 14th embodiment. Thus, the different part from the 14th embodiment will mainly be described, and an illustration or description of the parts common to the 14th embodiment is omitted.

The cover 26 is formed of a material, such as a synthetic resin material, which has heat resistance and adiathermancy, and has a lower thermal conductivity than metals or the like. The cover 26 has a right-angled triangular shape, as viewed from the lateral side. The cover 26 includes a near-side portion 81 (oblique-line portion) located on a side facing the vibration transmitting member main body 66, and a far-side portion 82 (base portion) provided on a side opposite to the near-side portion 81. As is clear from FIG. 26A and FIG. 26B, the length of the near-side portion 81 is greater than the length of the far-side portion 82.

Referring to FIG. 26A and FIG. 26B, the function of the medical device 11 of the present embodiment will be described. Before treating body tissue that is a treated target by using the medical device 11 of the present embodiment, the surgeon makes the vibration transmitting member main body 66 and jaw 24 reach the region of the treated target in the patient's body by the same method as in the first embodiment.

In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel. At this time, if the jaw 24 is set in the abutted position, the vibration transmitting member main body 66 bends and comes in contact with the cover 26, as indicated by a two-dot-and-dash line in FIG. 26A. In this state, the heat of the vibration transmitting member main body 66 is conducted to the cover 26. The amount of heat conducted to the far-side portion is less than the amount of heat conducted to the near-side portion. In addition, the length of the near-side portion 81 is greater than the length of the far-side portion 82. Thus, in the near-side portion, the amount of base material, which undergoes thermal expansion, is also greater.

Thus, in the present embodiment, the thermal expansion amount of the near-side portion 81 is greater than the thermal expansion amount of the far-side portion 82, and, as illustrated in FIG. 26B, the vicinity of the first distal portion 36 of the cover 26 bends in a manner to warp in a direction away from the vibration transmitting member main body 66. Thereby, on the first distal portion 36 side, the cover 26 is separated from the vibration transmitting member main body 66, and the temperature of the cover 26 is prevented from further rising.

According to the present embodiment, the cover 26 includes the near-side portion 81 located on the side facing the vibration transmitting member main body 66, and the far-side portion 82 provided on the side opposite to the near-side portion 81 and configured to have a lower thermal expansion amount than the near-side portion 81. According to this configuration, when a temperature rise occurs in the cover 26 by the heat conducted from the vibration transmitting member main body 66, the cover 26 can be bent in a manner to warp in a direction away from the vibration transmitting member main body 66. Thus, the cover 26 can be separated from the vibration transmitting member main body 66. Thereby, a further temperature rise in the cover 26 can be prevented.

16th Embodiment

Referring to FIG. 27A and FIG. 27B, a medical device of a 16th embodiment will be described. The medical device 11 of the 16th embodiment differs from that of the 15th embodiment in that the cover 26 is formed of two kinds of materials, and the shape of the cover 26 is different. However, the other parts are common to the 15th embodiment. Thus, the different part from the 15th embodiment will mainly be described, and an illustration or description of the parts common to the 15th embodiment is omitted.

As illustrated in FIG. 27A, the cover 26 extends in a tongue shape in a direction along the vibration transmitting member main body 66. The cover 26 covers that side of the vibration transmitting member main body 66, which is opposite to the side thereof facing the jaw 24. The cover 26 includes a near-side portion 81 located on a side facing the vibration transmitting member 21, and a far-side portion 82 provided on a side opposite to the near-side portion 81. The near-side portion 81 is formed of a general synthetic resin material, for example, a super engineering plastic such as polysulfone (PSF) or polyetheretherketone (PEEK). The far-side portion 82 is formed of a material which is obtained by mixing a low-thermal-expansion filler, such as a zirconium phosphate-based compound, into a general synthetic resin material, for example, a super engineering plastic such as polysulfone (PSF) or polyetheretherketone (PEEK). Thus, the thermal expansion amount of the near-side portion 81 is greater than the thermal expansion amount of the far-side portion 82. A small gap is provided between the cover 26 and the vibration transmitting member main body 66.

Referring to FIG. 27A, the function of the medical device 11 of the present embodiment will be described. Before treating body tissue that is a treated target by using the medical device 11 of the present embodiment, the surgeon makes the vibration transmitting member 21 and jaw 24 reach the region of the treated target in the patient's body by the same method as in the first embodiment.

In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel. At this time, although heat is conducted from the vibration transmitting member main body 66 to the cover 26, the thermal expansion amount of the near-side portion 81 is greater than the thermal expansion amount of the far-side portion 82. Thus, in the present embodiment, the thermal expansion amount of the near-side portion 81 becomes greater than the thermal expansion amount of the far-side portion 82, and, as illustrated in FIG. 27B, the vicinity of the first distal portion 36 of the cover 26 bends in a manner to warp in a direction away from the vibration transmitting member main body 66. Thereby, on the first distal portion 36 side, the cover 26 is separated from the vibration transmitting member main body 66, and the temperature of the cover 26 is prevented from further rising.

According to the present embodiment, the cover 26 includes the near-side portion 81 located on the side facing the vibration transmitting member 21, and the far-side portion 82 provided on the side opposite to the near-side portion 81 and configured to have a lower thermal expansion amount than the near-side portion 81. According to this configuration, when a temperature rise occurs in the cover 26 by the heat conducted from the vibration transmitting member main body 66, the cover 26 can be separated from the vibration transmitting member main body 66. Thereby, a further temperature rise in the cover 26 can be prevented.

17th Embodiment

Referring to FIG. 28, a medical device of a 17th embodiment will be described. The medical device 11 of the 17th embodiment differs from that of the first embodiment in that the structure of the cover 26 is different. However, the other parts are common to the first embodiment. Thus, the different part from the first embodiment will mainly be described, and an illustration or description of the parts common to the first embodiment is omitted.

The cover 26 extends in a tongue shape in a direction along the vibration transmitting member 21. The cover 26 covers that side of the vibration transmitting member 21, which is opposite to the side thereof facing the jaw 24. The base material of the cover 26 is formed of a material, such as a synthetic resin material, which has heat resistance and adiathermancy, and has a lower thermal conductivity than metals or the like.

A heat radiation member 84 for radiating heat is buried in the inside of the cover 26. The heat radiation member 84 is formed of a metallic material with good thermal conductivity, such as copper or aluminum, in a linear shape or a plate shape. The heat radiation member 84 is thermally connected to the sheath 22. A small gap is provided between the cover 26 and the vibration transmitting member main body 66.

Referring to FIG. 28, the function of the medical device 11 of the present embodiment will be described. In the medical device 11 of the present embodiment, the surgeon makes the vibration transmitting member main body 66 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel.

At this time, although heat is conducted from the vibration transmitting member main body 66 to the cover 26, the heat conducted to the cover 26 is always released to the sheath 22 side via the heat radiation member 84. Thus, the temperature of the cover 26 is prevented from further rising.

According to the present embodiment, the heat, which is conducted from the vibration transmitting member main body 66, can be released to the sheath 22 side via the heat radiation member 84. Thus, the temperature of the cover 26 is prevented from further rising.

18th Embodiment

Referring to FIG. 29, a medical device 11 of an 18th embodiment will be described. The medical device 11 of the 18th embodiment differs from that of the first embodiment in that the structure of the cover 26 is different. However, the other parts are common to the first embodiment. Thus, the different part from the first embodiment will mainly be described, and an illustration or description of the parts common to the first embodiment is omitted.

The cover 26 extends in a tongue shape in a direction along the vibration transmitting member 21. The cover 26 covers that side of the vibration transmitting member main body 66, which is opposite to the side thereof facing the jaw 24. The cover 26 includes a near-side portion 81 located on a side facing the vibration transmitting member main body 66, and a far-side portion 82 provided on a side opposite to the near-side portion 81. The near-side portion 81 is formed of a porous material with a high adiathermancy. The far-side portion 82 is formed of a general synthetic resin material. A small gap is provided between the cover 26 and the vibration transmitting member main body 66.

Referring to FIG. 29, the function of the medical device 11 of the present embodiment will be described. In the medical device 11 of the present embodiment, the surgeon makes the vibration transmitting member main body 66 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel.

At this time, although heat is conducted from the vibration transmitting member main body 66 to the cover 26, the heat conduction is hindered in the near-side portion 81 with adiathermancy of the cover 26, and the heat is prevented from being conducted to the far-side portion 82 side of the cover 26.

According to the present embodiment, a temperature rise can be prevented from occurring in the far-side portion 82 of the cover 26. Even if the far-side portion 82 of the cover 26, when not intended, comes in contact with nearby body tissue of the treated target during the treatment, it is possible to prevent the nearby body tissue from being adversely affected by heat.

19th Embodiment

Referring to FIG. 30A and FIG. 30B, a medical device 11 of a 19th embodiment will be described. The medical device 11 of the 19th embodiment differs from that of the first embodiment in that the shape of the cover 26 is different. However, the other parts are common to the first embodiment. Thus, the different part from the first embodiment will mainly be described, and an illustration or description of the parts common to the first embodiment is omitted.

The cover 26 has a substantially C-shaped cross section. The cover 26 covers that side of the vibration transmitting member main body 66, which is opposite to the side thereof facing the jaw 24. The cover 26 includes side wall portions 85 (near-side portions) which are opposed to the side surfaces of the vibration transmitting member main body 66, and a bottom wall portion 86 (far-side portion) that is opposed to the back surface of the vibration transmitting member main body 66, which is opposite to the treatment surface 21A of the vibration transmitting member main body 66. The cover 26 is integrally formed of a material, such as a synthetic resin material, which has heat resistance and adiathermancy, and has a lower thermal conductivity than metals or the like. A small gap is provided between the cover 26 and the vibration transmitting member main body 66. The dimension of a gap between the side wall portion 85 and the vibration transmitting member 21 is less than the dimension of a gap between the bottom wall portion 86 and the vibration transmitting member 21.

Referring to FIG. 30A and FIG. 30B, the function of the medical device 11 of the present embodiment will be described. In the medical device 11 of the present embodiment, the surgeon makes the vibration transmitting member main body 66 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel. At this time, although heat is conducted from the vibration transmitting member main body 66 to the cover 26, the amount of heat, which is conducted from the vibration transmitting member main body 66 to the side wall portions 85, is greater than the amount of heat, which is conducted from the vibration transmitting member main body 66 to the bottom wall portion 86. Thus, the thermal expansion amount of the side-wall portions 85 is greater than the thermal expansion amount of the bottom wall portion 86, and, as illustrated in FIG. 30B, the cover 26 bends, on the first distal portion 36 side, in a manner to warp in a direction away from the vibration transmitting member main body 66. Thereby, on the first distal portion 36 side, the cover 26 is separated from the vibration transmitting member main body 66, and the temperature of the cover 26 is prevented from further rising.

According to the present embodiment, the cover 26 includes the near-side portions located on the side facing the vibration transmitting member main body 66, and the far-side portion provided on the side opposite to the near-side portions and configured to have a lower thermal expansion amount than the near-side portions. According to this configuration, when a temperature rise occurs in the cover 26 by the heat conducted from the vibration transmitting member main body 66, the cover 26 can be separated from the vibration transmitting member 21. Thereby, a further temperature rise in the cover 26 can be prevented.

20th Embodiment

Referring to FIG. 31A to FIG. 31E, a medical device 11 of a 20th embodiment will be described. The medical device 11 of the 20th embodiment differs from that of the first embodiment in that the shape of the cover 26 is different. However, the other parts are common to the first embodiment. Thus, the different part from the first embodiment will mainly be described, and an illustration or description of the parts common to the first embodiment is omitted.

The cover 26 extends in a tongue shape in a direction along the vibration transmitting member 21. The cover 26 covers that side of the vibration transmitting member main body 66, which is opposite to the side thereof facing the jaw 24. The cover 26 is formed of a material, such as a synthetic resin material, which has heat resistance and adiathermancy, and has a lower thermal conductivity than metals or the like. The first proximal portion 37 of the cover 26 is provided with a small-thickness portion 87 which has a less thickness dimension than the other of the cover 26. Thus, in the present embodiment, the section modulus of the cover 26 decreases in the vicinity of the first proximal portion 37. A small gap is provided between the cover 26 and the vibration transmitting member main body 66.

Referring to FIG. 31A to FIG. 31E, the function of the medical device 11 of the present embodiment will be described. In the medical device 11 of the present embodiment, the surgeon makes the vibration transmitting member main body 66 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel.

The surgeon moves the jaw 24 from the spaced position 48 to the abutted position 47. At this time, the section modulus of the cover 26 decreases in the vicinity of the first proximal portion 37. Thus, by the urging force of the jaw 24, the vibration transmitting member main body 66 bends toward the cover 26. In addition, even when a relatively small load is applied to the cover 26, the cover 26 can bend in the direction of the arrow in a manner to follow the bending of the vibration transmitting member main body 66.

According to the present embodiment, the cover 26 includes the small-thickness portion 87, and can bend in the manner to follow the bending of the vibration transmitting member main body 66. Thus, the contact pressure between the cover 26 and the vibration transmitting member main body 66 is reduced, and it is possible to prevent the heat of the vibration transmitting member main body 66 from being easily conducted to the cover 26 side.

Figure 31A:
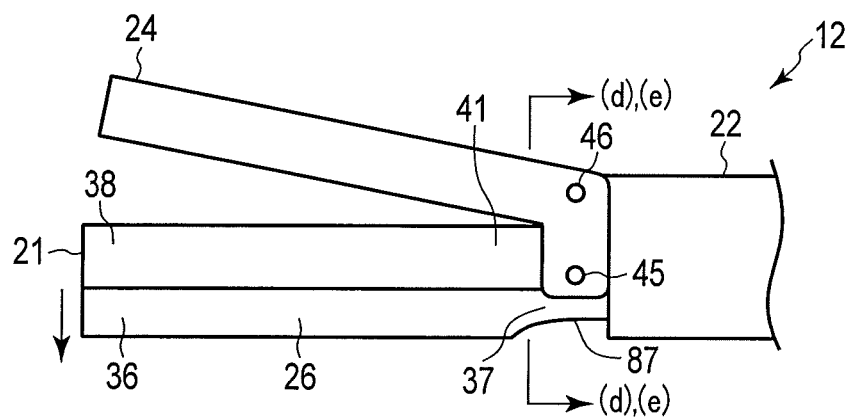
FIG. 31A is a side view illustrating a vibration transmitting member, a jaw and a cover of a medical device of a 20th embodiment.
Figure 31B:
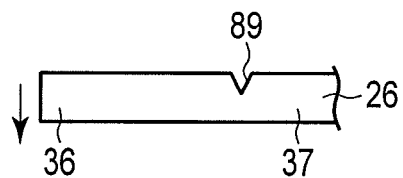
FIG. 31B is a side view illustrating a cover of a first modification of the medical device of the 20th embodiment.
Figure 31C:
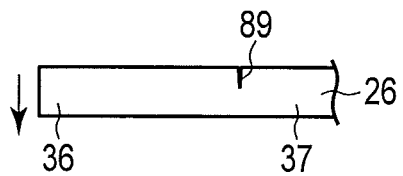
FIG. 31C is a side view illustrating a cover of a second modification of the medical device of the 20th embodiment.

FIG. 31B illustrates a first modification of the 20th embodiment, and FIG. 31C illustrates a second modification thereof. As in the first modification and second modification, also when a groove portion 89 with a large width or a small width is provided on that surface of the cover 26 which is opposed to the vibration transmitting member main body 66, the section modulus of the cover 26 can be decreased in the vicinity of the first proximal portion 37. Like the cover 26 of FIG. 31A, the cover 26 bends in the direction of the arrow by a small load, and the heat conduction to the cover 26 side can be reduced.

Figure 31D:
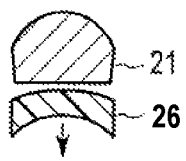
FIG. 31D is a cross-sectional view illustrating a cover of a third modification of the medical device of the 20th embodiment.
Figure 31E:
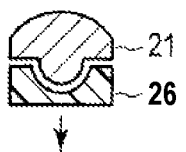
FIG. 31E is a cross-sectional view illustrating a cover of a fourth modification of the medical device of the 20th embodiment.

Besides, FIG. 31D illustrates a third modification of the 20th embodiment, and FIG. 31E illustrates a fourth modification thereof. In the third modification, the cross-sectional shape of the vicinity of the first proximal portion 37 of the cover 26 is arcuate. In the fourth modification, the vicinity of the first proximal portion 37 of the cover 26 has such a cross-sectional shape that a central part is recessed in an arcuate shape. Even with the cross-sectional shape as in the third modification or fourth modification, the section modulus of the cover 26 can be decreased in the vicinity of the first proximal portion 37. Like the cover 26 of FIG. 31A, the cover 26 bends in the direction of the arrow by a small load, and the heat conduction to the cover 26 side can be reduced.

21st Embodiment

Figure 32A:
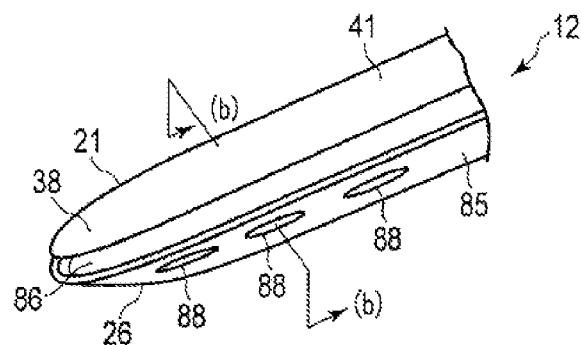
FIG. 32A is a perspective view illustrating a vibration transmitting member, a jaw and a cover of a medical device of a 21st embodiment.
Figure 32B:
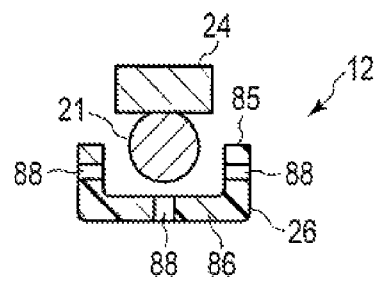
FIG. 32B is a cross-sectional view taken along line (b)-(b) in FIG. 32A.

Referring to FIG. 32A and FIG. 32B, a medical device of a 21st embodiment will be described. The medical device of the 21st embodiment differs from that of the first embodiment in that the shape of the cover 26 is different. However, the other parts are common to the first embodiment. Thus, the different part from the first embodiment will mainly be described, and an illustration or description of the parts common to the first embodiment is omitted.

The cover 26 has a substantially C-shaped cross section. The cover 26 covers that side of the vibration transmitting member 21, which is opposite to the side thereof facing the jaw 24. The cover 26 includes side wall portions 85 which are opposed to the side surfaces of the vibration transmitting member main body 66, and a bottom wall portion 86 that is opposed to the back surface of the vibration transmitting member main body 66, which is opposite to the treatment surface 21A of the vibration transmitting member main body 66. The cover 26 is integrally formed of a material, such as a synthetic resin material, which has heat resistance and adiathermancy, and has a lower thermal conductivity than metals or the like. A small gap is provided between the cover 26 and the vibration transmitting member main body 66.

Through-holes 88 are provided to penetrate each of the side wall portions 85 and bottom wall portion 86 in the thickness direction. The through-hole 88 is formed, for example, in an elliptic shape elongated a direction along the longitudinal direction C of the vibration transmitting member main body 66.

Referring to FIG. 32A and FIG. 32B, the function of the medical device 11 of the present embodiment will be described. In the medical device 11 of the present embodiment, the surgeon makes the vibration transmitting member main body 66 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel.

At this time, a piece of body tissue, coagulated blood, etc., which occurred by the treatment, are discharged to the outside through the through-holes 88. It is thus possible to prevent the piece of body tissue from being burnt and adhering to the vibration transmitting member 21, and being caught between the vibration transmitting member main body 66 and the cover 26.

According to the present embodiment, the through-holes 88 are formed in the side wall portions 85 and bottom wall portion 86 of the cover 26. According to this configuration, a piece of body tissue, coagulated blood, etc. do not stay between the vibration transmitting member main body 66 and the cover 26, and it is possible to prevent such a piece of body tissue, etc. from being burnt and adhering to the vibration transmitting member 21, and being caught (coagulated) between the vibration transmitting member main body 66 and the cover 26.

22nd Embodiment

Figure 33A:
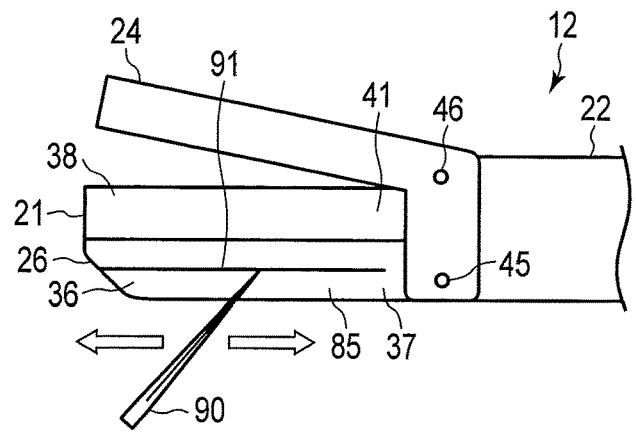
FIG. 33A is a side view illustrating a vibration transmitting member, a jaw and a cover of a medical device of a 22nd embodiment.
Figure 33B:
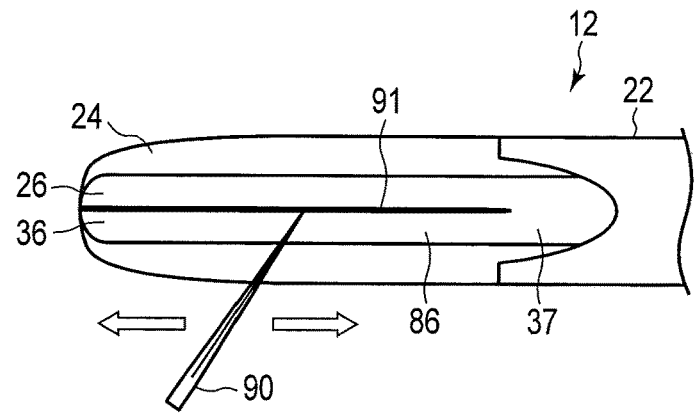
FIG. 33B is a bottom view, as viewed from below in FIG. 33A.

Referring to FIG. 33A and FIG. 33B, a medical device of a 22nd embodiment will be described. A medical device 11 of the 22nd embodiment differs from that of the 21st embodiment in that a slit 91, in place of the through-holes 88, is provided in the cover 26. However, the other parts are common to the 21st embodiment. Thus, the different part from the 21st embodiment will mainly be described, and an illustration or description of the parts common to the 21st embodiment is omitted.

FIG. 33A illustrates a state in which the cover 26 is viewed from the lateral side. FIG. 33B illustrates a state in which the cover 26 is viewed from below. Like the 21st embodiment, the cover 26 has a substantially C-shaped cross section. The cover 26 covers that side of the vibration transmitting member main body 66, which is opposite to the side thereof facing the jaw 24. The cover 26 includes side wall portions 85 which are opposed to the side surfaces of the vibration transmitting member main body 66, and a bottom wall portion 86 that is opposed to the back surface of the vibration transmitting member main body 66, which is opposite to the treatment surface 21A of the vibration transmitting member main body 66. The cover 26 is integrally formed of a material, such as a synthetic resin material, which has heat resistance and adiathermancy, and has a lower thermal conductivity than metals or the like. A small gap is provided between the cover 26 and the vibration transmitting member 21.

In the present embodiment, in place of the through-holes 88, a slit 91 extending in the longitudinal direction C of the vibration transmitting member main body 66 is provided in each of the side wall portions 85 and bottom wall portion 86.

Referring to FIG. 33A and FIG. 33B, the function of the medical device 11 of the present embodiment will be described. In the medical device 11 of the present embodiment, the surgeon makes the vibration transmitting member main body 66 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel.

At this time, a part of a piece of body tissue, coagulated blood, etc., which occurred by the treatment, enters the inside of the cover 26. However, by using a needle-like member 90 as needed, the surgeon can discharge to the outside the piece of body tissue staying in the inside of the cover 26, by advancing and retreating, such as by stroking, the needle-like member 90 which is passed through the slit 91. It is thus possible to prevent the piece of body tissue from being burnt and adhering to the vibration transmitting member main body 66, and being caught (coagulated) between the vibration transmitting member main body 66 and the cover 26.

According to the present embodiment, the slits 91 are provided in the cover 26. Thus, even when the piece of body tissue or the like stays in the inside of the cover 26, the inside of the cover 26 can be cleaned through the slits 91. Thereby, it is possible to prevent the piece of body tissue or the like from being burnt and adhering to the vibration transmitting member main body 66, and being caught between the vibration transmitting member main body 66 and the cover 26.

23rd Embodiment

Figure 34A:
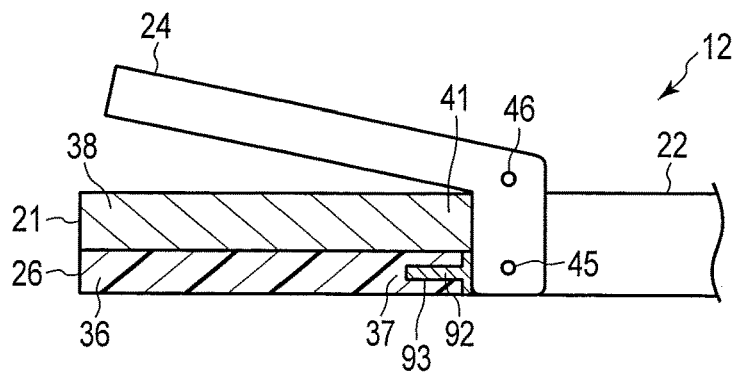
FIG. 34A is a partially broken-out side view illustrating a vibration transmitting member, a jaw and a cover of a medical device of a 23rd embodiment.
Figure 34B:
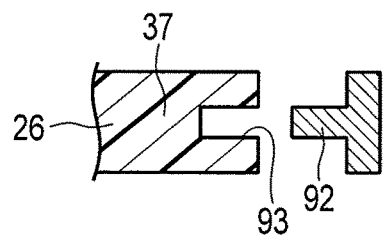
FIG. 34B is a cross-sectional view illustrating a state in which the cover of FIG. 34A is removed.

Referring to FIG. 34A and FIG. 34B, a medical device of a 23rd embodiment will be described. A medical device 11 of the 23rd embodiment differs from that of the first embodiment in that the cover 26 is attachable/detachable. However, the other parts are common to the first embodiment. Thus, the different part from the first embodiment will mainly be described, and an illustration or description of the parts common to the first embodiment is omitted.

As illustrated in FIG. 34A, the cover 26 includes a first distal portion 36 which is located on a distal side in the longitudinal direction C of the vibration transmitting member 21, a first proximal portion 37 which is located on an opposite side to the first distal portion 36, and a pin-shaped adapter 92 which is fixed to the sheath 22. The cover 26 extends in a tongue shape in a direction along the vibration transmitting member 21. Although not illustrated, a small gap is provided between the cover 26 and the vibration transmitting member main body 66.

The cover 26 covers that side of the vibration transmitting member main body 66, which is opposite to the side thereof facing the jaw 24. The cover 26 is formed of a material, such as a synthetic resin material, which has heat resistance and adiathermancy, and has a lower thermal conductivity than metals or the like. A hole portion 93, which is engageable with the adapter 92, is provided in the first proximal portion 37. The cover 26 is attachable/detachable via the adapter 92 and hole portion 93.

Referring to FIG. 34A and FIG. 34B, the function of the medical device 11 of the present embodiment will be described. In the medical device 11 of the present embodiment, the surgeon makes the vibration transmitting member main body 66 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel.

At this time, a part of a piece of body tissue, coagulated blood, etc., which occurred by the treatment, enters the inside of the cover 26. However, by detaching the cover 26 as needed, as illustrated in FIG. 34B, the surgeon can eliminate the piece of body tissue staying between the vibration transmitting member main body 66 and the cover 26. It is thus possible to prevent the piece of body tissue from being burnt and adhering to the vibration transmitting member main body 66, and being caught between the vibration transmitting member main body 66 and the cover 26.

According to the present embodiment, since the cover 26 is attachable/detachable, the piece of body tissue or the like, which stays between the vibration transmitting member main body 66 and the cover 26, can be removed. Thereby, it is possible to prevent the piece of body tissue or the like from being burnt and adhering to the vibration transmitting member main body 66, and being caught between the vibration transmitting member main body 66 and the cover 26.

24th Embodiment

Figure 35:
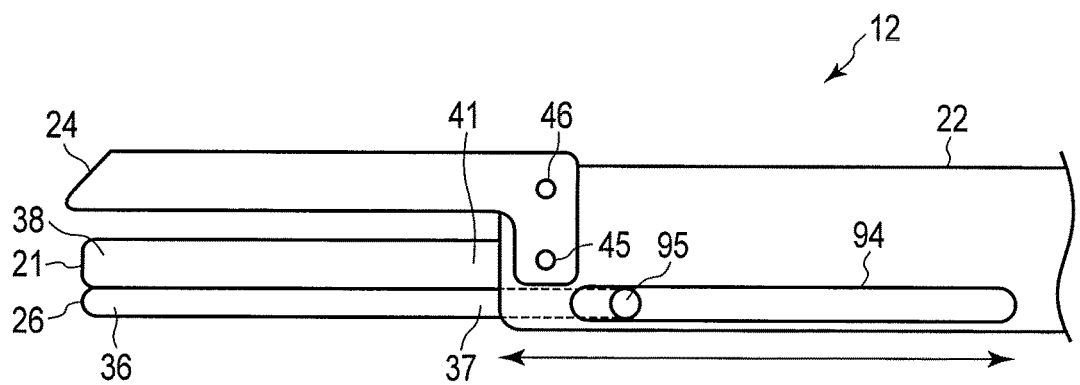
FIG. 35 is a partially broken-out side view illustrating a vibration transmitting member, a jaw and a cover of a medical device of a 24th embodiment.

Referring to FIG. 35, a medical device 11 of a 24th embodiment will be described. The medical device 11 of the 24th embodiment differs from that of the 23rd embodiment in that the cover 26 is slidable. However, the other parts are common to the 23rd embodiment. Thus, the different part from the 23rd embodiment will mainly be described, and an illustration or description of the parts common to the 23rd embodiment is omitted.

The sheath 22 includes a slide hole 94 for sliding, the slide hole 94 extending in the longitudinal direction C of the vibration transmitting member 21.

The cover 26 includes a first distal portion 36 which is located on a distal side in the longitudinal direction C of the vibration transmitting member 21, a first proximal portion 37 which is located on an opposite side to the first distal portion 36, and an operation lever 95 which is provided on the first proximal portion 37 and is passed through the slide hole 94. The cover 26 is operated via the operation lever 95, and thereby the cover 26 can advance and retreat between a projection position where the cover 26 projects from the sheath 22, and a stored position where the cover 26 is stored in the sheath.

When the cover 26 is in the projection position, the cover 26 extends in a tongue shape in a direction along the vibration transmitting member 21. At this time, although not illustrated, a small gap is provided between the cover 26 and the vibration transmitting member 21. The cover 26 covers that side of the vibration transmitting member main body 66, which is opposite to the side thereof facing the jaw 24. The cover 26 is formed of a material, such as a synthetic resin material, which has heat resistance and adiathermancy, and has a lower thermal conductivity than metals or the like.

Referring to FIG. 35, the function of the medical device 11 of the present embodiment will be described. In the medical device of the present embodiment, the surgeon makes the vibration transmitting member main body 66 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel.

At this time, a part of a piece of body tissue, coagulated blood, etc., which occurred by the treatment, enters the inside of the cover 26. However, as indicated by an arrow in FIG. 35, by operating the operation lever 95 as needed and storing the cover 26 into the sheath 22, the surgeon can eliminate the piece of body tissue staying between the vibration transmitting member main body 66 and the cover 26 which is in the projection position. It is thus possible to prevent the piece of body tissue from being burnt and adhering to the vibration transmitting member main body 66, and being caught between the vibration transmitting member main body 66 and the cover 26.

According to the present embodiment, since the cover 26 is attachable/detachable, the piece of body tissue or the like, which stays between the vibration transmitting member main body 66 and the cover 26, can be removed. Thereby, it is possible to prevent the piece of body tissue or the like from being burnt and adhering to the vibration transmitting member main body 66, and being caught (coagulated) between the vibration transmitting member main body 66 and the cover 26.

25th Embodiment

Figure 36:
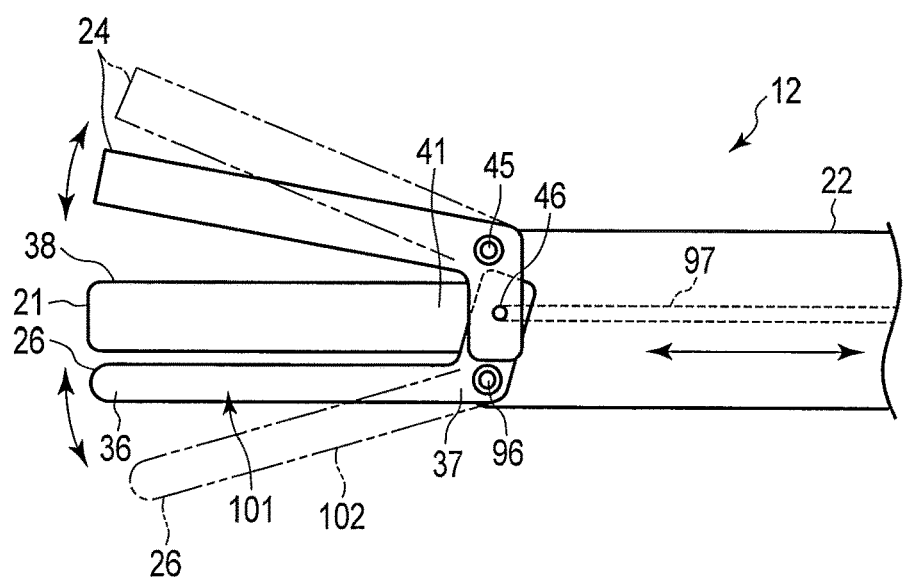
FIG. 36 is a side view illustrating a vibration transmitting member, a jaw and a cover of a medical device of a 25th embodiment.

Referring to FIG. 36, a medical device of a 25th embodiment will be described. A medical device 11 of the 25th embodiment differs from that of the first embodiment in that the cover 26 is rotatable. However, the other parts are common to the first embodiment. Thus, the different part from the first embodiment will mainly be described, and an illustration or description of the parts common to the first embodiment is omitted.

The sheath 22 includes, at its distal portion, a first support pin 45 which rotatably supports the jaw 24, and a second support pin 96 which rotatably supports the cover 26.

A driving shaft portion 97 is provided to be advanceable/retreatable in the inside of the sheath 22. The driving shaft portion 97 includes, at its distal end, a driving pin 46 for opening and closing the jaw 24 and cover 26. The driving shaft portion 97 advances and retreats in accordance with the operation of the movable handle 17, and can separate the jaw 24 and cover 26 from the vibration transmitting member main body 66, can abut the jaw 24 on the vibration transmitting member main body 66, and can make the cover 26 approach the vibration transmitting member 21.

Referring to FIG. 36, the function of the medical device 11 of the present embodiment will be described. In the medical device 11 of the present embodiment, the surgeon makes the vibration transmitting member main body 66 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue (and blood vessel).

In addition, when increasing the spacing between body tissues and ablating the body tissues, the surgeon can utilize not only an opening movement of the jaw 24 but also an opening movement of the cover 26.

According to the 25th embodiment, the cover 26 is rotatable between a first position 101 near the vibration transmitting member main body 66 and a second position 102 spaced apart from the vibration transmitting member main body 66, in accordance with the movement of the jaw 24 between the abutted position 47 and spaced position 48. Thus, when increasing the spacing between body tissues in the treatment, the surgeon can utilize not only the opening movement of the jaw 24 but also the opening movement of the cover 26. Thereby, the work efficiency of the surgeon can be improved, and the time of surgery can be shortened.

26th Embodiment

Referring to FIG. 37, a medical device of a 26th embodiment will be described. A medical device 11 of the 26th embodiment differs from that of the first embodiment in that the cover 26 can be evacuated from the vicinity of the vibration transmitting member main body 66. However, the other parts are common to the first embodiment. Thus, the different part from the first embodiment will mainly be described, and an illustration or description of the parts common to the first embodiment is omitted.

The cover 26 is formed of, for example, a synthetic resin material with rubber-like elasticity in an elongated bag shape. In addition, the cover 26 is reformed in a spirally wound shape, and, in a natural state, the cover 26 has the spirally wound shape as indicated by a solid line in FIG. 37. A fluid, such as water or air, can be injected in the inside of the cover 26. In the state in which the fluid is injected, the cover 26 can project (swell), as indicated by a broken line in FIG. 37, in a manner to cover that side of the vibration transmitting member main body 66, which is opposite to the side thereof facing the jaw 24. On the other hand, if the fluid is removed from the inside of the cover 26, the cover 26 can change into the spiral shape as indicated by the solid line in FIG. 37 and can be evacuated (moved to an evacuation position 103) from the vicinity of the vibration transmitting member main body 66.

Referring to FIG. 37, the function of the medical device 11 of the present embodiment will be described. In the medical device 11 of the present embodiment, the surgeon makes the vibration transmitting member 21 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel. In the meantime, during a coagulation/incision treatment or a coagulation treatment of the body tissue or blood vessel, the cover 26 is filled with the fluid, and is swollen to such a position as to cover the vibration transmitting member main body 66.

At this time, a part of a piece of body tissue, coagulated blood, etc., which occurred by the treatment, enters between the vibration transmitting member main body 66 and the cover 26 which is in the projection position. However, by evacuating the cover 26 as needed, as indicated by the solid line in FIG. 37, the surgeon can eliminate the piece of body tissue staying between the vibration transmitting member main body 66 and the cover 26. In addition, when the vibration transmitting member main body 66 and the jaw 24 are inserted into a small gap between body tissues, the cover 26 is evacuated, and thereby the cover 26 does not hinder the work.

According to the present embodiment, since the cover 26 can be evacuated to the evacuation position 103, the piece of body tissue or the like between the vibration transmitting member main body 66 and the cover 26 can be removed. Thereby, it is possible to prevent the piece of body tissue, etc. from being burnt and adhering to the vibration transmitting member main body 66. Besides, by evacuating the cover 26 to the evacuation position, the vibration transmitting member main body 66 and the jaw 24 can be inserted into even a small gap between body tissues. Thus, the work efficiency of the surgeon can be improved, and the time of surgery can be shortened.

27th Embodiment

Referring to FIG. 38A and FIG. 38B, a medical device of a 27th embodiment will be described. A medical device 11 of the 27th embodiment differs from that of the 26th embodiment in that the cover 26 is not reformed in a spirally wound shape. However, the other parts are common to the 26th embodiment. Thus, the different part from the 26th embodiment will mainly be described, and an illustration or description of the parts common to the 26th embodiment is omitted.

The cover 26 is formed of, for example, a synthetic resin material with rubber-like elasticity in an elongated bag shape. In the present embodiment, unlike the 26th embodiment, the cover 26 is not reformed in the spirally wound shape. A fluid, such as water or air, can be injected in the inside of the cover 26. In the state in which the fluid is injected, the cover 26 can swell, as illustrated in FIG. 38B, in a manner to cover that side of the vibration transmitting member main body 66, which is opposite to the side thereof facing the jaw 24. On the other hand, if the fluid is removed from the inside of the cover 26, the cover 26 can be contracted, as illustrated in FIG. 38A.

Referring to FIG. 38A and FIG. 38B, the function of the medical device 11 of the present embodiment will be described. In the medical device 11 of the present embodiment, the surgeon makes the vibration transmitting member main body 66 and jaw 24 reach the region of the treated target in the patient's body by the same method as in the first embodiment. In addition, like the first embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel. In the meantime, during a coagulation/incision treatment or a coagulation treatment of the body tissue or blood vessel, the cover 26 is filled with the fluid, and is swollen to such a position as to cover the vibration transmitting member main body 66.

In this case, when the vibration transmitting member main body 66 and the jaw 24 are inserted into a small gap between body tissues, the fluid is removed from the cover 26, and the cover 26 is contracted. Thereby, the vibration transmitting member main body 66 and the jaw 24 can be inserted into even a small gap between body tissues.

According to the present embodiment, since the cover 26 can be contracted as needed, the vibration transmitting member main body 66 and the jaw 24 can be inserted into even a small gap between body tissues. Thereby, the cover 26 does not hinder the work, the work efficiency of the surgeon can be improved, and the time of surgery can be shortened.

28th Embodiment

Referring to FIG. 39A and FIG. 39B, a medical device of a 28th embodiment will be described. A medical device 11 of the 28th embodiment differs from that of the 24th embodiment in that the direction of movement of the cover 26 is different. However, the other parts are common to the 24th embodiment. Thus, the different part from the 24th embodiment will mainly be described, and an illustration or description of the parts common to the 24th embodiment is omitted.

The cover 26 includes a first portion 104 which corresponds to one side surface of the vibration transmitting member main body 66, and a second portion 105 which corresponds to the other side surface of the vibration transmitting member main body 66. The first portion 104 and second portion 105 can rotate around the vibration transmitting member 21, about an axis extending in the longitudinal direction C of the vibration transmitting member 21. The first portion 104 and second portion 105 are attached in a manner to be rotatable relative to the outer peripheral surface of the sheath 22.

The surgeon rotates the cover 26 by fingers or the like. Thereby, the cover 26 can be rotated between a storage position 106 where the cover 26 covers the vibration transmitting member 21 as illustrated in FIG. 39A, and an exposure position 107 where the cover 26 exposes the vibration transmitting member 21 as illustrated in FIG. 39B. The cover 26 is formed of a material, such as a synthetic resin material, which has heat resistance and adiathermancy, and has a lower thermal conductivity than metals or the like.

Referring to FIG. 39A and FIG. 39B, the function of the medical device 11 of the present embodiment will be described. In the medical device 11 of the present embodiment, the surgeon makes the vibration transmitting member main body 66 and jaw 24 reach the region of the treated target in the patient's body by the same method as in the first embodiment. In addition, the surgeon moves the first portion 104 and second portion 105 of the cover 26 to the exposure position 107. Like the 24th embodiment, in the region of the treated target, the surgeon can clamp the body tissue between the vibration transmitting member main body 66 and the jaw 24, and can perform, by operating the energy operation input button 27, the coagulation and incision or only the coagulation of the body tissue and blood vessel.

After the treatment is finished, the surgeon can rotate once again and move the first portion 104 and second portion 105 of the cover 26 to the storage position 106.

According to the present embodiment, the vibration transmitting member 21 can be stored or exposed by the cover 26 as needed.

(First Modification)

Referring to FIG. 40A and FIG. 40B, a first modification of the medical device of the 28th embodiment will be described. A medical device 11 of the first modification differs from that of the 28th embodiment in that the means for moving the cover 26 between the storage position 106 and exposure position 107 is different. However, the other parts are common to the 28th embodiment. Thus, the different part from the 28th embodiment will mainly be described, and an illustration or description of the parts common to the 28th embodiment is omitted.

The cover 26 includes a thin-film covering member 111 and a shape memory alloy 112 which is passed through the inside of the covering member 111. In the cover 26, a stimulus (thermal stimulus or electric stimulus) is applied to the shape memory alloy 112. Thereby, the cover 26 can move between the storage position 106 where the cover 26 covers the vibration transmitting member main body 66 as illustrated in FIG. 40A, and the exposure position 107 where the cover 26 exposes the vibration transmitting member main body 66 as illustrated in FIG. 40B. According to the present modification, like the 28th embodiment, the surgeon can store or expose the vibration transmitting member main body 66 by the cover 26, as needed.

(Second Modification)

Figure 41B:
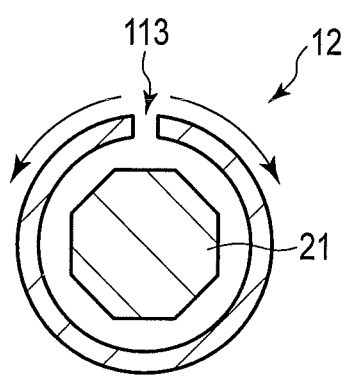
FIG. 41B is a cross-sectional view illustrating a direction in which the cover is opened when the cover of FIG. 41A is moved to the exposure position.

Referring to FIG. 41A and FIG. 41B, a second modification of the medical device of the 28th embodiment will be described. A medical device 11 of the second modification differs from that of the 28th embodiment in that the method for moving the cover 26 between the storage position 106 and exposure position 107 is different. However, the other parts are common to the 28th embodiment. Thus, the different part from the 28th embodiment will mainly be described, and an illustration or description of the parts common to the 28th embodiment is omitted.

The cover 26 is formed in a cylindrical shape, and a longitudinal slit 113 is provided in a part of the cover 26. The surgeon turns over the cover 26 at the position of the longitudinal slit 113 by using fingers. Thereby, the surgeon can adjust the position of the cover 26 between the storage position 106 where the cover 26 covers the vibration transmitting member 21 as illustrated in FIG. 41A, and the exposure position where the cover 26 exposes the vibration transmitting member 21. According to the present modification, like the 28th embodiment, the surgeon can store or expose the vibration transmitting member main body 66 by the cover 26, as needed.

The present invention is not limited to the above-described embodiments, and modifications may be implemented where necessary, without departing from the spirit of the invention. Moreover, needless to say, the medical devices 11 of the above-described embodiments can be combined to constitute a single medical device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

REFERENCE SIGNS LIST

11 . . . Medical device, 12 . . . Handpiece, 21 . . . Vibration transmitting member, 24 . . . Jaw, 26 . . . Cover, 36 . . . First distal portion, 37 . . . First proximal portion, 38 . . . Second distal portion, 47 . . . Abutted position, 48 . . . Spaced position, 52 . . . Curved portion, 53 . . . Recess portion, 55 . . . Second cover, 61 . . . First surface, 62 . . . Second surface, 63 . . . Evacuation mechanism, 65 . . . Separate position, 73 . . . Channel, 81 . . . Near-side portion, 82 . . . Far-side portion, C . . . Longitudinal direction.

What is claimed is:

1. A medical device comprising:
a vibration transmitting member configured to transmit vibration for a treatment;
a jaw configured to move between an abutted position where the jaw abuts on the vibration transmitting member, and a spaced position where the jaw is spaced apart from the vibration transmitting member;
a cover disposed such that the vibration transmitting member is interposed between the cover and the jaw, and the cover is configured such that a first distal portion located at a distal end of the cover comes in contact with the vibration transmitting member when the jaw is located in the abutted position, the cover including a recess portion configured to receive a protrusion of the vibration transmitting member such that the protrusion is configured to extend into the recess portion and be interposed between opposing sides of the recess portion; and
a small-thickness portion provided on a proximal portion of the cover, the small-thickness portion having a thickness that is less than a thickness of a remainder of the cover, wherein
the cover is configured to bend so as to follow the vibration transmitting member when the vibration transmitting member is bent.

2. The medical device of claim 1, wherein the cover is formed of a material having heat resistance and adiathermancy.

3. The medical device of claim 1, wherein the vibration transmitting member is configured to bend by being pushed by the jaw when the jaw is in the abutted position and come in contact with the first distal portion of the cover.

4. The medical device of claim 1, wherein the cover includes:
a first proximal portion disposed in a direction along the vibration transmitting member with a gap provided between the first proximal portion and the vibration transmitting member;
the first distal portion abutted on the vibration transmitting member; and an intermediate portion configured to continuously connect the first proximal portion and the first distal portion.

5. The medical device of claim 1, further comprising:
a first surface disposed on a vibration transmitting member side and opposed to the cover; and
a second surface disposed on a cover side and opposed to the vibration transmitting member,
wherein at least one of the first surface and the second surface has a low frictional property.

6. The medical device of claim 1, wherein the cover is configured to cover the vibration transmitting member at a position separate from a second distal portion disposed at a distal end of the vibration transmitting member.

7. The medical device of claim 1, wherein the recess portion is formed into the cover at a position between the proximal portion of the cover and the distal end of the cover, the recess portion having an arcuate cross-section recessed into an inner surface of the cover facing an inner surface of the vibration transmitting member and complementing the protrusion, the protrusion having a semicircular cross-section and being formed on an inner surface of the vibration transmitting member.

* * * * *